US006488618B1

(12) United States Patent
Paolitto et al.

(10) Patent No.: US 6,488,618 B1
(45) Date of Patent: Dec. 3, 2002

(54) CORONARY STABILIZER FOR PERFORMING BEATING HEART SURGERY

(75) Inventors: Anthony Paolitto, St. Leonard; Valerio Valentini, Montreal; Raymond Cartier, Town of Mount Royal, all of (CA)

(73) Assignee: Coroneo, Inc., Montreal (CA)

( * ) Notice: Subject to any disclaimer, the term of this patent is extended or adjusted under 35 U.S.C. 154(b) by 0 days.

(21) Appl. No.: 09/550,168

(22) Filed: Apr. 14, 2000

(51) Int. Cl.$^7$ .................................................. A61F 2/00
(52) U.S. Cl. ........................................................ 600/37
(58) Field of Search ........................... 600/37, 213, 232, 600/235, 231, 210, 204, 205, 228; 606/205, 207, 210; 81/418, 419, 424.5–426.5; 152/209; 36/59

(56) References Cited

U.S. PATENT DOCUMENTS

| | | | | |
|---|---|---|---|---|
| 5,529,101 A | * | 6/1996 | Croyle et al. | 152/209 |
| 6,036,641 A | * | 5/2000 | Taylor et al. | 600/231 |
| 6,063,021 A | * | 5/2000 | Hossain et al. | 600/37 |
| 6,132,370 A | * | 10/2000 | Furnish et al. | 600/235 |
| 6,213,941 B1 | * | 4/2001 | Benetti et al. | 600/235 |
| 6,241,655 B1 | * | 6/2001 | Riess | 600/37 |

FOREIGN PATENT DOCUMENTS

WO    WO-98/27869    *    7/1998

* cited by examiner

Primary Examiner—Eric F. Winakur
Assistant Examiner—David McCrosky

(57) ABSTRACT

The present invention provides an improved coronary stabilizer for use in cardiac surgery, and more particularly during a coronary artery bypass graft (CABG) surgery performed directly on a beating heart. The coronary stabilizer is comprised of a body contact member and a handle. An opening or arterial window is provided in the body contact member, in order to allow surgical access to a target coronary artery which is exposed through said arterial window. In a first embodiment, the body contact member is a bifurcated hand comprising first and second body contacting portions, for placement alongside a target artery. Each of said body contacting portions is contoured to provide a coronary stabilizer with a substantially saddle-shaped body contacting surface, thereby tending to promote the extrusion of immobilized myocardium tissue through the arterial window generally disposed between first and second contacting portions. The coronary stabilizer according to this first embodiment preferably has a pull-type handle and is best suited to immobilize a posterior or inferior portion of the beating heart surface, during posterior coronary artery revascularizations. In a second embodiment, a coronary stabilizer with a substantially cup-shaped body contacting surface is provided and preferably configured with a push-type handle. It is best suited to immobilize an anterior portion of the beating heart surface, during anterior coronary artery revascularizations. The coronary stabilizers according to the present invention are preferably configured with an array of surgical wire attachment fittings for engaging an elastic surgical wire, that may be looped about a target artery, in order to create a substantially bloodless surgical field during a beating heart anastomosis. The contact surfaces of the coronary stabilizers preferably have a tread or tissue-engaging texture which may be configured to provide a tractive gradient.

20 Claims, 11 Drawing Sheets

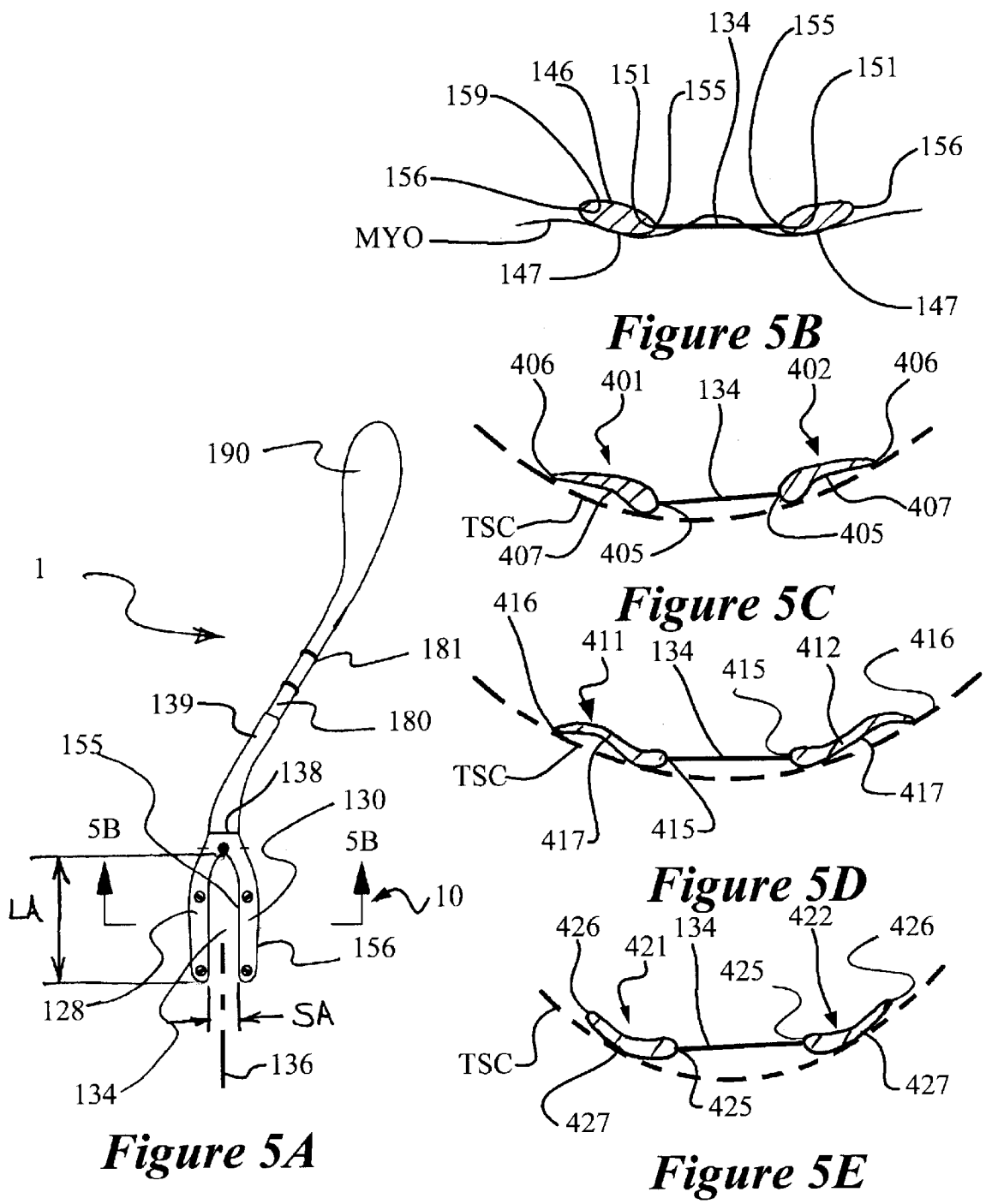

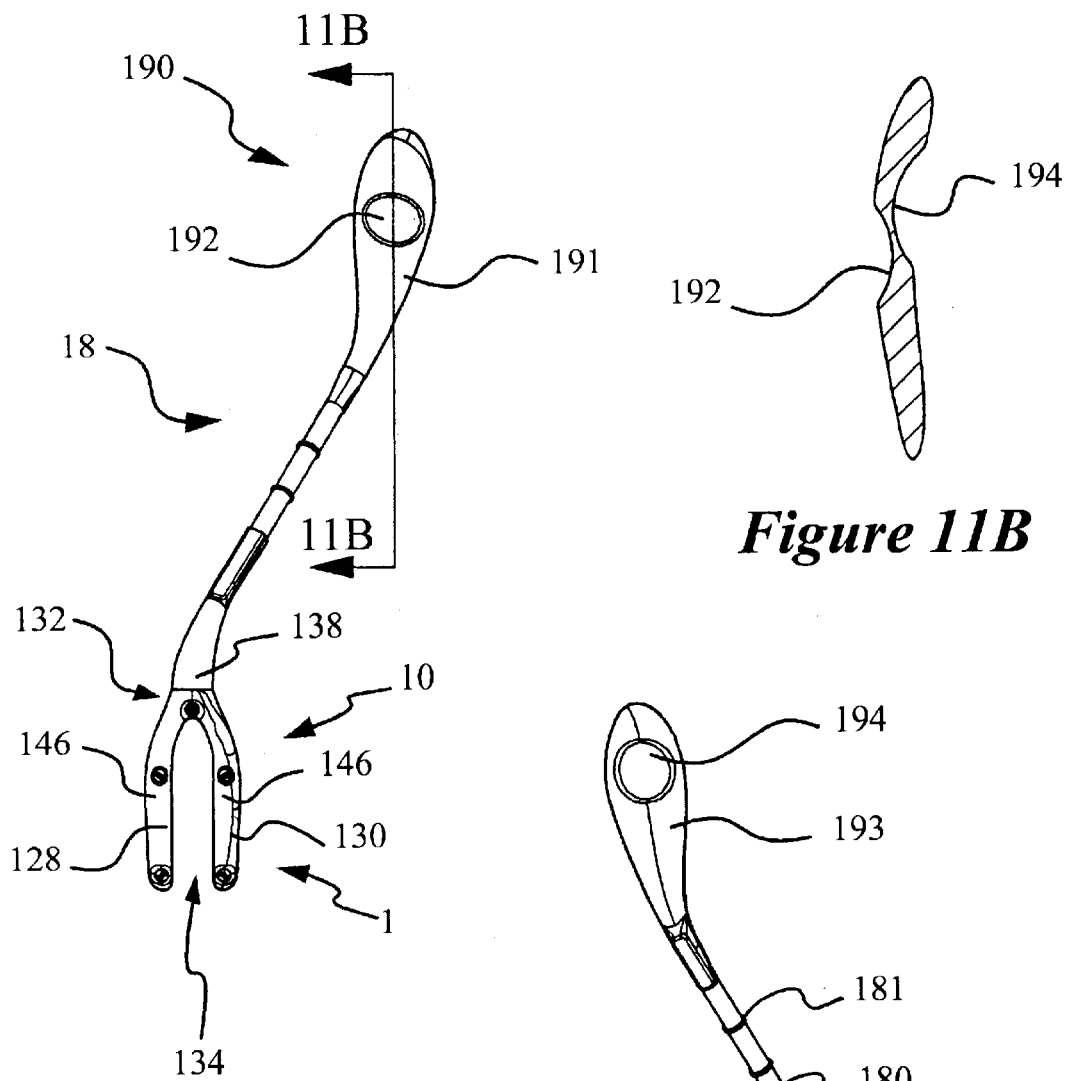
Figure 11A
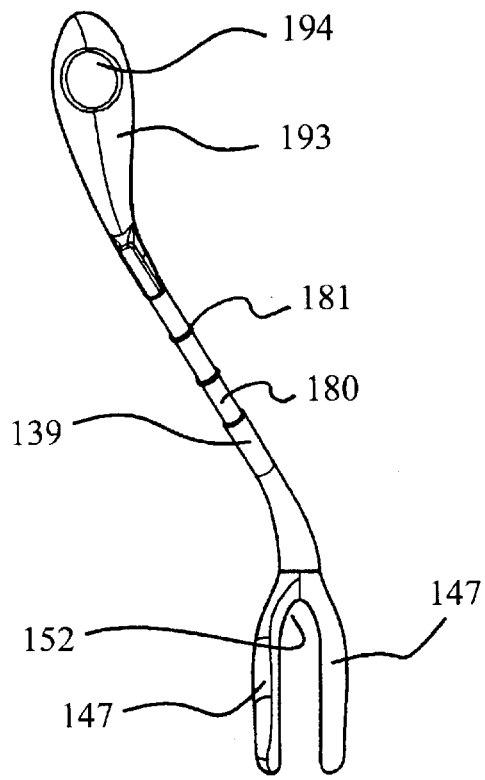
Figure 11B
Figure 11C

CORONARY STABILIZER FOR PERFORMING BEATING HEART SURGERY

FIELD OF THE INVENTION

The present invention relates to the field of surgical apparatus, and more specifically to tissue stabilizers such as may be used, for example, to perform cardiac surgery on a beating heart.

BACKGROUND OF THE INVENTION

The growing interest in less invasive surgery has placed emphasis on cardiac surgery as well. The main difference in heart surgery with respect to other organ surgeries, gall bladder for instance, is that the beating motion of the heart tends to complicate the delicate surgical interventions that are normally performed in cardiac surgery.

Cardiac surgery has been traditionally performed with the support of a cardio-pulmonary machine, whereby the patient's blood is oxygenated outside the body through extracorporeal circulation (ECC). This allows the surgeon to perform surgical procedures on a perfectly still heart, while the patient's life support is maintained by cardiopulmonary assistance. During traditional coronary artery bypass graft (CABG) surgery, the surgeon or assistant may manually or otherwise manipulate the arrested heart into a position and orientation that yields the best access to a target coronary artery requiring a bypass graft, or coronary artery revascularization.

Recently, in an aim to render CABG surgery less invasive to the patient, beating heart CABG surgery is being developed whereby ECC, one of the most invasive aspects of cardiac surgery, is eliminated and coronary artery revascularization is performed directly on the beating heart. One of the challenges in performing beating heart CABG surgery lies in positioning and orienting the beating heart in order to obtain access to the inferior and posterior artery beds, while aiming to minimize physiologically undesirable effects such as hemodynamic instability, arrhythmia, or a precipitous drop in arterial pressure, that may occur as a result of such beating heart manipulation.

Another challenge lies in locally immobilizing at least a portion of the beating heart surface, or myocardium, in the vicinity of the target coronary artery requiring the bypass graft, or anastomosis, in an attempt to simulate the arrested myocardium normally operated on in traditional CABG surgery. To this end, a variety of movement restraining devices, or coronary stabilizers, have been and continue to be developed. Most coronary stabilizers have a contact member with a substantially planar body contact surface. The contact surface is typically interrupted by an opening, or arterial window, in the contact member in order to obtain access to the target artery exposed within the arterial window. The immobilization load applied by the coronary stabilizer to the heart tends to cause a protrusion or extrusion of myocardium tissue through the arterial window. The tissue extrusion obtained with a substantially planar contact surface applying a modest immobilization load on the heart, is generally quite small. Furthermore, with disposable-type plastic stabilizers, the contact member must be sufficiently thick to provide the required stiffness and rigidity in stabilizer design to adequately immobilize the contacted heart surface. As such, the generally small tissue extrusion through the arterial window may not even extend in height above the top, or exposed surface, of the relatively thick plastic contact member. In an attempt to improve the amount of tissue extrusion to a desired level in height, above the exposed surface of the contact member, a significantly greater immobilization load must be applied to the substantially planar contact member. As a result, this tends to impose restraints on the beating heart that may considerably impede its normal beating function, and induce the onset of the physiologically undesirable effects described above.

In light of foregoing, it would be beneficial to have a coronary stabilizer with an advantageously contoured body contact surface that tends to induce, entrain or promote a considerable extrusion of a portion of immobilized heart tissue through its arterial window. It would be a further advantage if this extrusion could be accomplished while at least a part of said contact surface also substantially conforms to the natural curvature of the heart. It would be yet a further advantage if this extrusion could be achieved with minimum impact to a heart chamber situated below the immobilized myocardium, thereby reducing the potential distortions in heart valvulature, and preserving hemodynamic stability.

In beating heart surgery, the pulsating effect of the heart may tend to induce disengagement or slipping of the contacted myocardium tissue relative to the contact surface of the coronary stabilizer. It would be beneficial to have a coronary stabilizer that has an advantageously contoured body contact surface, whereby this surface is configured with a tread or tissue-engaging texture that tends to enhance its traction on the contacted myocardium tissue.

Tissue stabilizers are typically manipulated through a handle that is connected to the body contact member. Tissue stabilizers may be kept in place by manually grasping and holding fixed said handle. Preferably, however, tissue stabilizers such as coronary stabilizers employed during a beating heart bypass surgery, are kept in place by securing said handle to a substantially stable surgical platform, such as a chest retractor. Said handle is usually engaged with a positioning means which is itself engaged to said retractor. Most coronary stabilizers have a handle extending away in height from the contact member, and from the contacted body tissue when in use. Such a handle may be referred to as a push-type handle because, in operation, said handle will tend to be in compression, when exerting a force against a portion of the heart, with its contact member. As such, surgical access to the arterial window, and to the exposed target coronary artery therein, may be compromised by the presence of said handle located generally within the surgical workspace situated above the arterial window. Based on the foregoing, and especially for posterior coronary artery revascularizations, it would be beneficial to provide a coronary stabilizer with an advantageously contoured contact member, and with a pull-type handle. Said pull-type handle extends away from the target artery in a direction that is generally rearwardly of the portion of heart tissue surface containing the target artery. This may tend to enhance the surgical access to the arterial window, by leaving the working access view of the arterial window unobstructed. It may also tend to permit a surgeon to obtain access to a lower side, or posterior portion of the heart. Finally, it may also help in maintaining the position of the beating heart in a substantially vertical orientation, with the apex directed generally outward of the retracted chest cavity, as may be required in order to access the posterior territory of the heart.

In beating heart CABG surgery, the heart continues to pump blood throughout the surgical procedure since ECC is avoided. As a result, an incision created in a coronary artery tends to cause bleeding within the surgical field. Surgical wires, preferably elastic vascular loops are sometimes used, during at least a part of the surgical procedure, to constrict or ligate a target coronary artery that will be surgically revascularized. A vascular loop is generally placed around a target coronary artery, at a location upstream of the intended arteriotomy and subsequent anastomosis, thereby serving to restrict blood flow through said target artery. Another such vascular loop may be placed at a location downstream of said arteriotomy incision, tending to minimize backflow from collateral arteries. As a result, an arteriotomy and subsequent anastomosis may be performed on said target artery in a substantially bloodless surgical field while the patient's heart continues to beat. One such vascular loop, with integrally assembled tissue-piercing needle, is commercially available from Quest Medical, Inc. of Allen, Tex., under brand name "Retract-O-Tape™".

Some coronary stabilizers are configured with anchoring features to secure said vascular loops. These anchoring features generally protrude above the heart contact surface of the coronary stabilizer, and as such, a vascular loop is generally secured to said stabilizer in a location situated in height above the heart contact surface of said stabilizer. Encircling of the target artery with a vascular loop, and subsequently pulling and securing the ends of said vascular loop to the coronary stabilizer, will tend to at least partially constrict the target artery. It may also tend to further extrude, through the arterial window, the portion of myocardium tissue containing the encircled target artery. This further extrusion is generally in addition to the extrusion that results when a coronary stabilizer with an advantageously contoured contact surface is engaged with a myocardium tissue. In light of the foregoing, it would be a further advantage if a coronary stabilizer with contoured contact surface is also provided with an array of surgical wire attachment fittings for engaging a surgical wire.

It is an object of the present invention to provide a tissue stabilizer, and more specifically a coronary stabilizer well-suited for performing beating heart CABG surgery, which tends to promote the extrusion of a contacted and substantially immobilized heart tissue, through an arterial window in said coronary stabilizer.

It is another object of the present invention to provide a coronary stabilizer with an advantageously contoured body contact surface, that tends to maximize the amount of tissue extrusion through an arterial window, when a given stabilization load is applied by said coronary stabilizer.

It is another object of the present invention to tend to improve surgical access to a coronary artery, especially a deep intramyocardial artery, by providing a coronary stabilizer which tends to extrude said artery through an arterial window in said coronary stabilizer.

These and other objects of the present invention will become apparent from the description of the present invention and its preferred embodiments which follows.

BRIEF DESCRIPTION OF THE DRAWINGS

For better understanding of the present invention and to show more clearly how it may be carried into effect, reference will now be made by way of illustration and not of limitation to the accompanying drawings, which show an apparatus according to the preferred embodiments of the present invention, and in which:

FIG. 5A is a top view of the coronary stabilizer illustrated in FIG. 1 depicting an arterial window in the bi-furcated hand;

FIGS. 5B to 5C illustrate several variants of transverse cross-sections through the medial portions of first and second fingers with reference to the first embodiment of FIG. 5A, depicting the relationship between inner and outer periphery of medial portions;

FIGS. 11A to 11C illustrate the coronary stabilizer illustrated in FIG. 1 depicting a manipulation member.

DETAILED DESCRIPTION OF THE INVENTION

The features and principles of this invention can be applied, in whole or in part, to cardiac surgery, vascular surgery, or other types of surgery requiring the stabilization or immobilization of a body tissue with a surgical tool serving as a body tissue stabilizer, and subsequently requiring a surgical intervention to be performed on a portion of the stabilized or immobilized body tissue accessed through an opening in said body tissue stabilizer. This includes those surgeries in which a surgical intervention is performed on an anatomic conduit, contained substantially within a portion of the stabilized or immobilized body tissue, and accessed through an opening in said body tissue stabilizer. Anatomic conduits include arteries, veins, organ ducts, air passageways, body fluid vessels, or other like anatomic conduits. The description of the embodiments that follow will, however, be illustrated in the context of cardiac surgery, and more specifically to coronary artery bypass graft (CABG) surgery performed on a target coronary artery of a beating heart.

In part, the embodiments of this invention may advantageously be applied, if desired, to the heart contacting means or heart stabilizer tool described in copending U.S. patent applications: Ser. No. 08/940,766 filed on Sept. 30, 1997 in the names of Cartier and Paolitto and entitled "Sternum Retractor for Performing Bypass Surgery on a Beating Heart", and Ser. No. 09/316,133 filed on May 21, 1999 in the names of Paolitto et al. and entitled "Surgical Apparatus and Method" the contents of which is incorporated herein by reference. Alternatively, the embodiments of the present invention may also be applied, if desired, to other types of body tissue stabilizers or coronary stabilizers.

Figure 1:
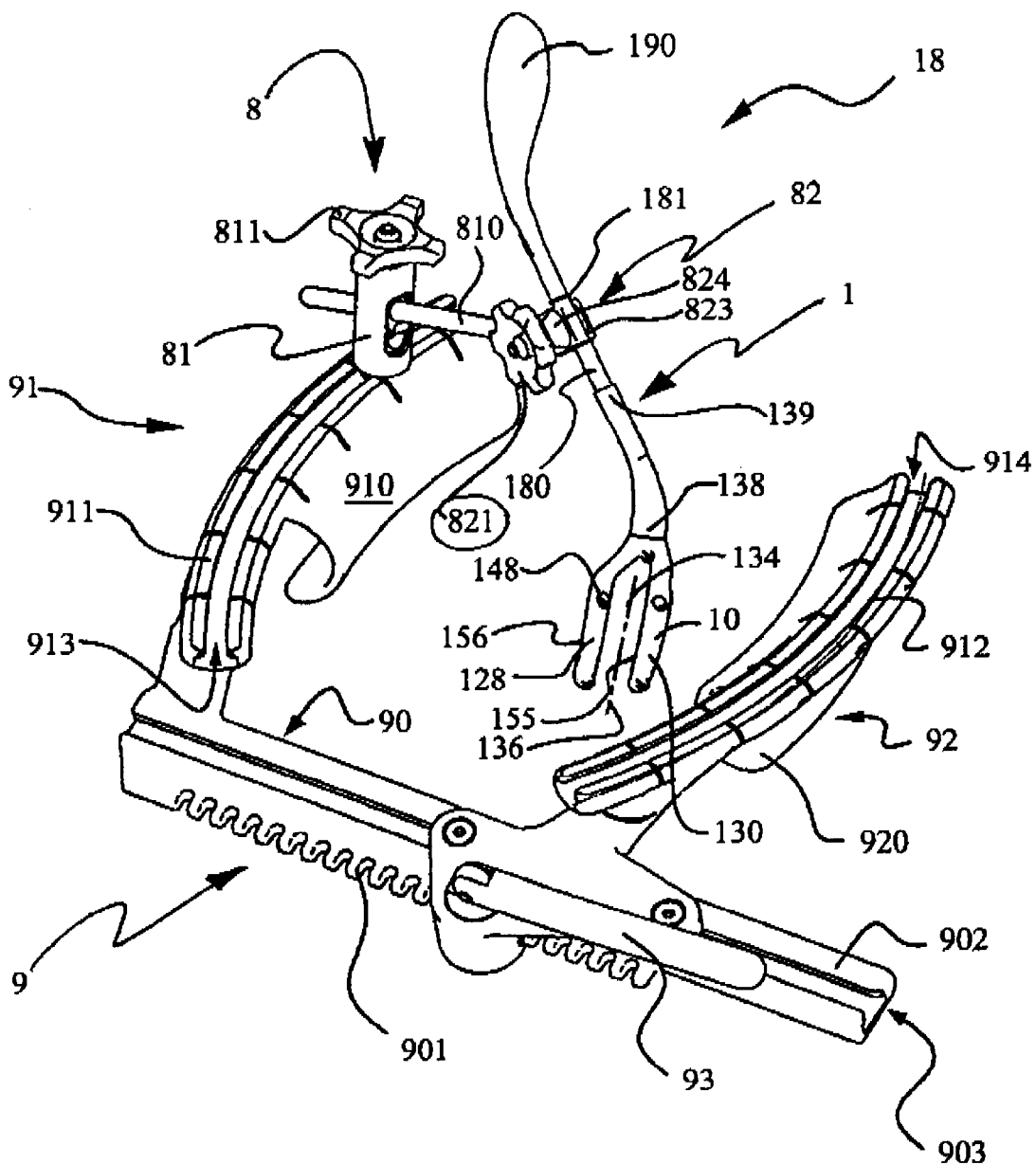
FIG. 1 is a perspective view illustrating a surgical apparatus with which a coronary stabilizer comprising a saddle-shaped body contact surface may be used, according to a first embodiment of the present invention.

By way of a general overview and with reference to FIG. 1, a surgical apparatus with which the invention may be used is comprised of three main components, a body tissue stabilizer tool in the nature of coronary stabilizer 1, a positioning means such as a multiple degree of freedom articulated arm assembly indicated generally as 8, and a substantially-stable surgical platform in the nature of chest retractor 9. Chest retractor 9 is illustrated in its deployed state, thereby providing the surgeon with access to a variety of body parts or internal coronary organs, which include the heart, the pericardium tissue, the aorta and vena cava, the coronary arteries and veins.

Chest retractor 9 includes four major parts: (i) an elongated rack bar 90, (ii) a first retractor spreader arm 91 being preferably fixed to rack bar 90, (iii) a second retractor spreader arm 92 being preferably movable with respect to the rack bar 90, and (iv) an actuator 93 for effecting movement of spreader arm 92 relative to spreader arm 91.

Retractor spreader arms 91 and 92 extend in a direction substantially transversely with regard to the rack bar 90, generally in the same direction therefrom and in a parallel orientation with respect to one another. The movable arm 92 may be displaced along the rack bar 90, and relative to the other spreader arm 91, preferably through the rotation of actuator 93 activated by the surgeon. Actuator 6 is operatively connected to the rack bar 90 and to the other spreader arm 92, and is translatable along the length of rack bar 90. This is preferably achieved by the engagement of a pinion mechanism (not shown) of actuator 93 with the rack teeth 901 on rack bar 90. Two retractor blades 910 and 920 are respectively provided with the retractor spreader arms 91 and 92, preferably disposed below the rack bar 90 when the chest retractor 9 is deployed on a patient. Retractor blades 910 and 920 may engage with and serve to retract, for instance, a portion of the patient's incised skin and the two halves of the patient's incised sternum, or ribcage, thereby exposing therebetween the patient's internal coronary organs. When viewing the retracted surgical opening from above the patient, retractor spreader arms 91 and 92 of the deployed chest retractor 9 have a generally arcuate orientation.

Chest retractor 9 advantageously comprises arcuate rails 911 and 912 along the top of spreader arms 91 and 92, respectively. Said rails 911 and 912 each configure an inverted T-slot arcuate passageway 913 and 914, respectively, preferably centrally located within said rails, and preferably extending throughout the entire arcuate length of said rails. A similar linear longitudinal rail 902 is preferably configured along the top of rack bar 90. Longitudinal rail 902 is also configured with an inverted T-slot longitudinal passage 903, preferably extending throughout its entire longitudinal length. These said rails form a mounting perimeter that can advantageously serve to engage a positioning means such as articulated arm assembly 8. The articulated arm assembly 8 may also be engaged with other types of substantially-stable surgical platforms such as a surgical table, surgical truss, or other like structures, provided such platforms are configured with the appropriate rails and passageways capable of engaging said articulated arm assembly.

Articulated arm assembly 8 is preferably comprised of a main, or shoulder joint indicated generally as 81 having a footing for engagement in one of passageways 913 (illustrated), 914, or 903. Shoulder joint 81 is also referred to as a first articulation member or cylindrical post. A first, or upper arm 810, is mounted in, and extends from, shoulderjoint 81 to a second, intermediate, or elbow joint, indicated generally as 82. Elbow joint 82 is also referred to as the second articulation member, or as the spherical clamp. Elbow joint 82 is a clamping assembly that interacts with a spheroidal distal end termination (not shown) in upper arm 810. Elbow joint 82 has a pair of left and right hand clamp side-frames 823 and 824, each having a spherical arc socket (not shown) for engaging said spheriodal termination in upper arm 810. At their respective distal ends, each of side-frames 823 and 824 has a jaw for tightening against shaft 18 of coronary stabilizer 1. Articulated arm assembly 8 is further described in above referenced U.S. patent applications Ser. Nos. 08/940,766 and 09/316,133. Alternate positioning means are also possible.

In this first embodiment, coronary stabilizer 1 has a body contacting member, in the nature of bi-furcated hand 10 for engaging a body part of a surgical patient, such as the heart; and a handle 18. Handle 18 is further comprised of a broadened and flattened manipulation member 190 and a cylindrical rod, or shaft 180, intermediate and rigidly connected to hand 10 and manipulation member 190. Shaft 180 is engageable in elbow joint 82 to perform the function of a second, lower, or forearm element when cooperating with articulated arm assembly 8.

Articulated assembly 8 provides a multitude of motion degrees of freedom that permits the coronary stabilizer 1 to be placed with acceptable accuracy in a wide range of positions and orientations within the surgical workspace. As such, the surgeon, or assistant, may place the coronary stabilizer 1 in a desired position and orientation relative to the patient's beating heart, during a surgical intervention such as a coronary artery revascularization. More specifically, shoulderjoint 81 provides the following motion degrees of freedom: the translation of upper arm 810 through shoulder joint 81 in a direction along the centerline axis of said arm 810; the angular articulation of upper arm 810 into and out of retracted chest cavity by changing the angle between the centerline axis of upper arm 810 and longitudinal axis of shoulder joint 81; the revolution of elbow joint 82 about the longitudinal axis of shoulder joint 81; and, the translation or sliding within passageways 913, 914 or 903 of shoulder joint 81. More specifically, elbow joint 82 provides the following motion degrees of freedom: the translation of shaft 180 through clamping side frames 823, 824; the rotation of coronary stabilizer 1 about the centerline axis of shaft 180; the revolution of contact member 10 about the centerline axis of upper arm 810; and, the angular articulation of coronary stabilizer 1 within a plane formed by the centerline axes of upper arm 810 and shaft 180.

The desired position and orientation of coronary stabilizer 1, relative to chest retractor 9, is secured through tensioning knobs 811 and 821. These said tensioning knobs serve to rigidly fix all the motion degrees of freedom available through shoulder joint 81 and elbow joint 82, respectively. As such, coronary stabilizer 1 provides a mechanical force that substantially immobilizes a portion of the patient's beating heart surface, or myocardium, in order to tend to facilitate a surgical intervention on a coronary artery thereof, while the rest of the patient's myocardium continues to beat.

As illustrated, shaft 180 is provided with an array of spaced, outwardly extending circumferential ridges 181 along its length. The spacing of these ridges is greater than the height dimension of side frames 823 and 824 of elbow joint 82. Two adjacent ridges cooperate to provide a bias to a motion degree of freedom, in this case the translation of shaft 180 through elbow joint 82. Said bias is variable within the limited range set by the two adjacent discrete ridges 181. While elbow joint 82 can tend to be manipulated with respect to the full range of all its other degrees of freedom, said bias provides a subset of the overall translation range of motion available along the entire length of shaft 180. The further apart the ridges, the wider is the limit in said bias within the entire translation range of motion along shaft 180. With tensioning knobs loose, ridges 181 also enable the surgeon to deploy the articulated arm 8 through the manipulation of manipulation member 190, which entrains the corresponding movements and articulations of elbow joint 82, and of shoulder joint 81, so that the contact member 10 may be set in a desired position and orientation relative to the patient's heart.

Figure 2:
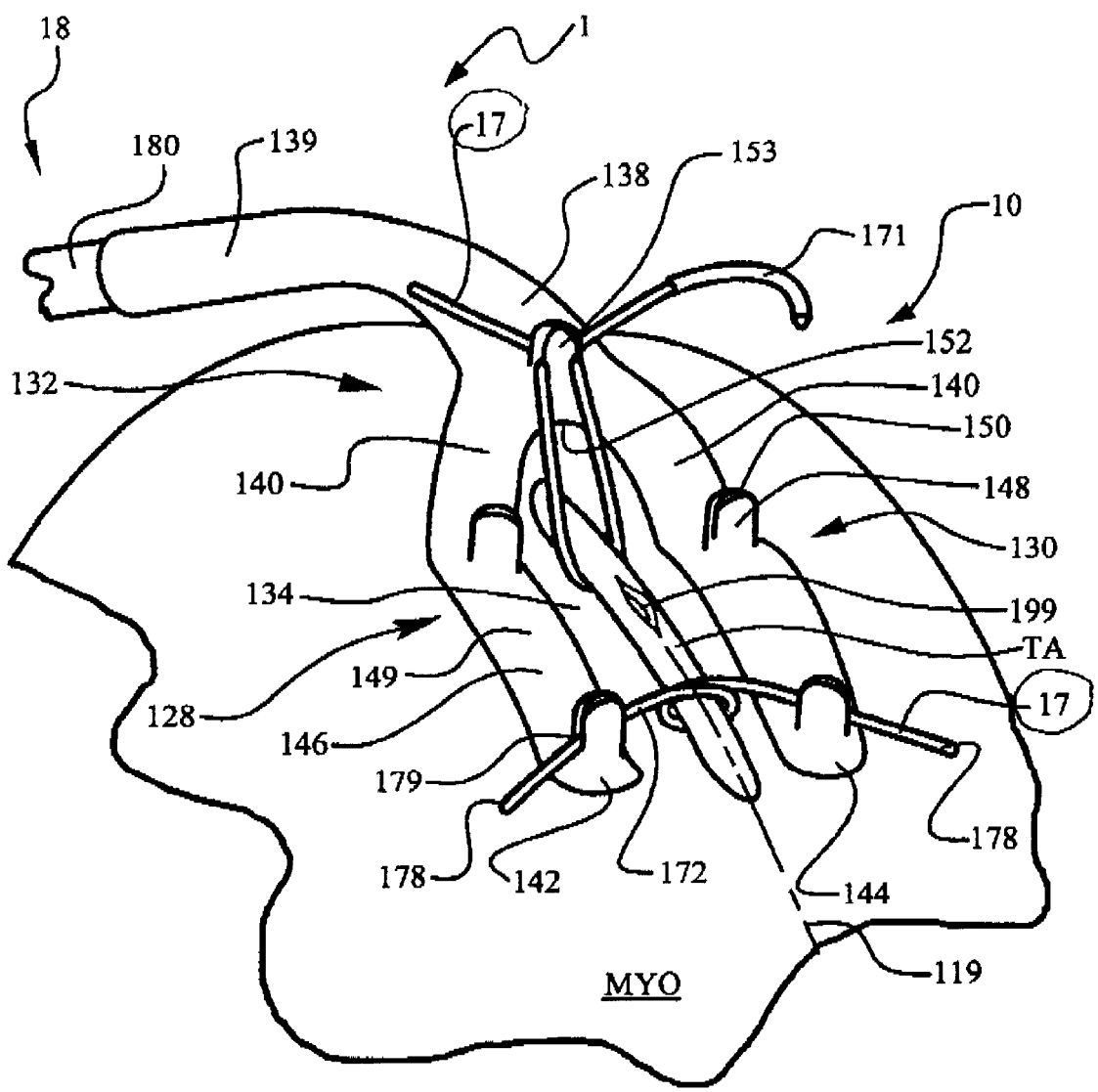
FIG. 2 is a partial perspective view of the coronary stabilizer illustrated in FIG. 1 depicting a body contact member in the nature of a bi-furcated hand engaged with the surface of a beating heart.

Referring now to FIG. 2, hand 10 has first and second body-contacting portions in the nature of a pair of fingers 128 and 130 joined by a yoke 132, the fingers defining between them a conduit window, or arterial window indicated generally as 134. As will be discussed in greater detail below, fingers 128 and 130 have a contoured contact surface, tending to suitably engage the anatomic curvature of the heart surface, and tending to promote the extrusion of myocardium tissue through the arterial window. Although fingers 128 and 130 are substantially parallel, this is not a necessary condition for defining an arterial window. An arterial window can have two, three, or four sides, or more, or can be defined by an oval, circular, elliptical or other shaped opening, whether having a closed periphery, or a periphery open at one or more sides. For instance, a coronary stabilizer may be comprised of two, or more, mating and demountable parts which form a substantially rectangular body-contact surface within which is a substantially rectangular arterial window. Fingers 128 and 130 are for placement to either side of an anatomic conduit, such as target coronary artery TA, with longitudinal axis 119 of target artery TA substantially aligned with the notional longitudinal axis 136 of arterial window 134.

Yoke 132 has a tapering root portion 138 connected to shaft 180 through an end fitting portion 139, and a bent, stepped portion 140 joining root portion 138 to the proximal ends of fingers 128 and 130. Root portion 138 is substantially offset from fingers 128, 130 in height away from contacted body tissue, in this case myocardium tissue MYO, to avoid pressing down on and occluding the target artery TA which is straddled by fingers 128, 130. U-shaped cut-out 152 is deep enough in stepped portion 140 to clear target artery TA straddled by said fingers. Fingers 128 and 130 are sometimes referred to as ski-like, in reference to their rounded distal tips 142 and 144 that are bent to stand away from the body contacted surface in use. Each of the fingers 128 and 130 has a first, or body contacting surface 147, and a second, non-contacting, exposed surface 146 for facing away from the body contacted surface while in use. Each of the fingers 128 and 130 has a medial portion generally spanning or extending between a rounded distal tip 142, or 144, and stepped portion 140. The body-contacting surface 147 generally extends over the said medial portion of each fingers 128 and 130.

As illustrated, an array of surgical wire attachment fittings, in the nature of upstanding hemispherical posts 148, are integrally cast with hand 10 to extend outwardly from exposed surface 146. Each post has at least one slot 150 for receiving therein a wire-like member, or surgical wire such as elastomeric vascular loop 17. As illustrated, each of the four slots 150 are preferably angled with respect to centerline 136 of arterial window 134. A fifth surgical wire attachment fitting, in the nature of upstanding hemispherical crotch post 153, is integrally cast to extend outwardly from exposed face, or exposed surface, of the outwardly stepped root portion 138 of yoke 132, adjacent the base of the U of U-shaped cut-out 152. Crotch post 153 is configured with two slots 154, substantially perpendicular in orientation to each other. Slots 150 and 154 are wide enough to admit a stretched portion of vascular loop 17, but when the stretching load is relieved, the engaged portion 179 of vascular loop 17 expands and is captured in the slot.

When a vascular loop 17 is anchored in two slots 150, or in two slots 154 of solitary crotch post 153, a functional length 172 spanning between said two anchoring slots results. A modest pull on an exposed end 178, in a direction generally away from arterial window 134, may increase the tension in the functional length 172, and adjust its position relative to slot 150, or slot 154. Alternatively, a modest pull in the opposite direction, generally towards arterial window 134, can decrease the tension in the functional length 172 and readjust its position relative to slot 150, or slot 154. As illustrated, coronary stabilizer 1 has two pairs of slotted posts 148, and a solitary crouch post 153. In use, hand 10 is preferably placed on the myocardium tissue, with fingers 128 and 130 located adjacent to, or to either side of, a target artery TA, and with one post 148 on each of fingers 128,130 located upstream of the intended surgical intervention site on the target artery, and the other post on each of said fingers located downstream of said intervention site. As such, one vascular loop 17 may be placed about a target artery TA, in a location upstream of arteriotomy incision 199, and secured to one solitary slotted post 153 (as shown) or secured to two slotted posts 148 on opposite sides of the arterial window 134 (not shown). Similarly, another such vascular loop 17 may be placed about target artery TA, in a location downstream of arteriotomy incision 199, and secured to two slotted posts 148 on opposite sides of the arterial window 134 as shown). Alternatively, other types of looping around a target artery TA, and subsequent securement to hand 10, may also be possible. For instance, a single slot of a single post, particularly in the position of crotch post 153, can be used to hold both ends of a surgical wire, thus permitting a loop to be formed about a vein or artery and anchored to a single point. In another example, one exposed end 178 of vascular loop 17 may be engaged in one slot 150, upstream of arteriotomy incision 199, while the other exposed end 178 is engaged in another slot 150 that is situated opposite the arterial window 134, and downstream of the arteriotomy incision 199.

Once the target artery TA is encircled with a vascular loop 17, pulling the two resulting lengths in a generally opposed direction induces a compressive load, or tourniquet effect, on the target artery. The desired artery constriction or ligation is achieved by maintaining the tension on each of the two free lengths of the vascular loop through their engagement in a slot 150, or 154, of coronary stabilizer 1. As such, the blood flow through the target artery TA may be restricted, or interrupted fully, to create a substantially bloodless surgical field after the arteriotomy incision is performed.

The vascular loop 17 may also be deployed to cooperate with contoured shape of hand 10, to further augment the extrusion of myocardium tissue through the arterial window, beyond the extrusion that is achieved solely by the contact of myocardium tissue with hand 10. In some instances, especially for a deep intramyocardial coronary artery, placing a length of vascular loop 17 under a target artery TA, and subsequently securing exposed lengths of vascular loop 17, under tension, to slots 150, or 154, tends to urge a portion of myocardium tissue, and target artery TA contained substantially therein, to stand proudly in arterial window 134, since said slots are located at a height above body-contacting surfaces 147.

Coronary stabilizer 1 serves to immobilize a portion of the patient's beating heart surface, or myocardium, relative to the remaining heart surface which is still substantially free to continue beating. A vascular loop 17 secured to attachment fittings on coronary stabilizer 1, in a manner described above, tends to isolate a target artery relative to the immobilized portion of myocardium, and tends to extrude it within the arterial window of said coronary stabilizer, beyond the extrusion achieved by the contacting of myocardium with coronary stabilizer 1. Furthermore, a vascular loop 17 looped about a target artery, in a manner described above, may serve to restrict blood flow through said target artery by controlling the amount of constriction or ligation.

Variations in surgical wire attachment fittings are also possible. For instance, a clip-type, a spring-type, a slotted-hemisphere-type, or a plate-like-type attachment fittings, may be mounted to extend outwardly from exposed surface 146, or from exposed surface of root portion 138, and serve to engage a portion of a surgical wire at a location extending proudly away in height away from body contact surface 147.

End fitting portion 139 of hand 10 is configured with a opening (not shown), extending along longitudinal axis of end fitting portion. Said opening is of a sufficient depth to mate with and receive the distal end of shaft 180. Shaft 180 is rigidly connected to hand 10 either through a weldment, a brazed joint, or a threaded interface between said opening and distal portion of shaft 180 engaged therein. Handle 18 and hand 10 may also be integrally cast as a one piece casting, or one piece coronary stabilizer 1. Alternatively, shaft 180 may be pivotingly connected to hand 10 through a ball and socket joint, or wrist joint, which may be rendered rigid through an actuation member which fixes the relative position of said ball and socket. Such ball and socket joints exist in numerous varieties and are well known in the art.

Considering handle 18 as representative, the manipulation member 190 itself is cast integrally with shaft 180. Manipulation member 190 has one surface 191 having a finger engagement dimple 192, and an opposite surface 193 having an opposed finger engagement dimple 194 (FIGS. 11A–11C). Cooperating dimples 192, 194 tend to enhance the traction between surgeon's fingers and the coronary stabilizer, especially when stabilizer is manipulated with surgical gloves in a wet surgical environment. Preferably, at least one depression-type feature or dimple is configured in manipulation member 190. Dimple 192 is ergonomically situated in top surface 191 to engage the surgeon's middle finger relative to the opposed dimple 194 which engages the surgeon's thumb. Alternatively, dimples may be replaced with grooves, a larger number of smaller dimples, or other like depression-type features intended to improve traction. Alternatively, the depression-type features may be replaced with protrusion-type features. For instance, an annular ridge that contours the surgeon's fingertips when they are in contact with the manipulation member, an array of raised pedestals, or other like protrusion-type features offering a raised geometry relative to surfaces 191 or 193. Referring again to FIG. 11A, manipulation member 190 preferably has a longitudinal axis generally aligned and offset to longitudinal axis 136 of arterial window 134. Through a proximal manipulation applied at manipulation member 190, the surgeon is able to distally position and orient hand 10.

Coronary stabilizer 1 is a pull-type tissue stabilizer that may tend to be suited for posterior or inferior coronary artery revascularizations on a beating heart, as described below. A pull-type stabilizer is so named because, in operation, shaft 180 will tend to be in tension, when exerting a force to manipulation member 190 of handle 18 against, for example, a portion of the heart. A steep angled pull handle, that is, one which is substantially perpendicular relative to contact member 10, will tend to have a greater proportion of its load in tension than a cantilever-like shallow angled pull-type handle. A handle of this type will tend to extend away from the target artery in a direction that is generally rearwardly of the target artery surface of the heart. This may tend to enhance the surgical access to the arterial window, by leaving the working access view of the arterial window unobstructed. This is clearly illustrated in FIG. 2. It may also tend to permit a surgeon to obtain access to a lower side, or posterior portion of the heart.

Figure 3A:
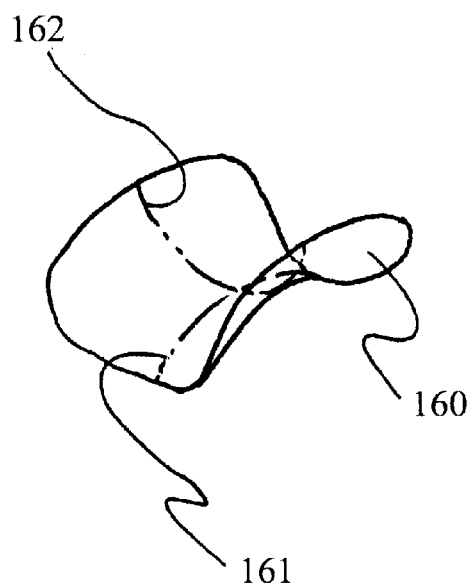
FIG. 3A is a schematic representation of a saddle-shaped surface which helps define the body contact surface of the coronary stabilizer illustrated in FIG. 1.
Figure 3B:
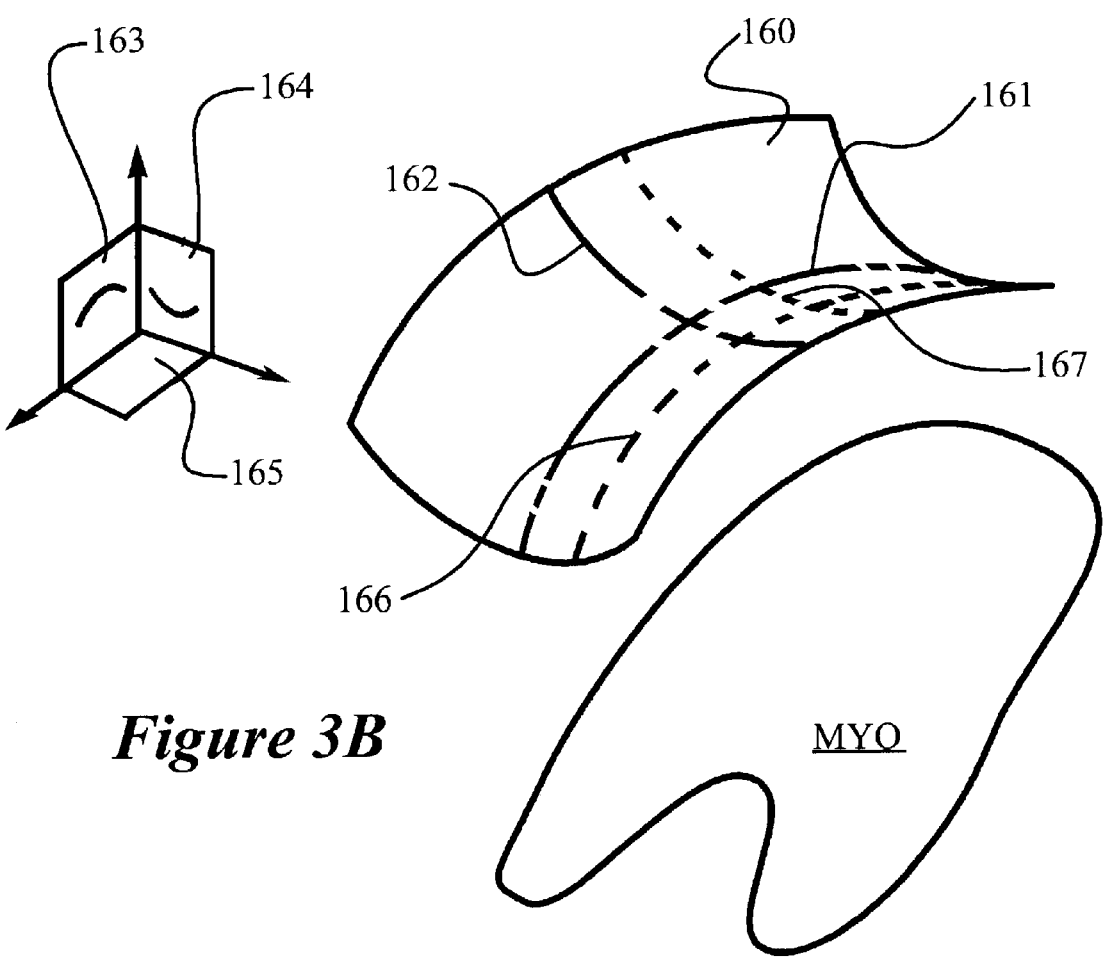
FIG. 3B is an enlarged view of the saddle-shaped surface illustrated in FIG. 3A depicting a number of reference contours and section planes.

With reference to FIGS. 3A and 3B, the geometry of the contact surface 147 of hand 10 will now be described in greater detail. Surface 160 depicts an infinitesimally-thin, substantially saddle-shaped surface. Lengthwise, it is characterized or defined by a longitudinal axis, longitudinal contour, or curved spine 161, which also longitudinally bisects said surface 160. Widthwise, it is characterized by a transverse axis, transverse contour, or curved rib section 162, which also transversely bisects said surface 160. Curved spine 161 generally lies within a plane 163, and when surface 160 is placed in contact with an underlying body tissue, schematically illustrated and labeled MYO, it has a concave orientation relative to said tissue. Curved rib section 162 generally lies in another plane 164, and when surface 160 is placed in contact with body tissue MYO, it has a convex orientation relative to said tissue. A third plane 165, is also defined as being tangent to curved rib section 162 at the point of intersection between curved spine 161 and curved rib section 162. Planes 163, 164, and 165 are perpendicular to each other.

If saddle-shaped surface 160 is cut by a section plane that is offset and parallel to plane 163, a longitudinal section curve, indicated generally as 166, will result. Longitudinal section curve 166 will be similar to longitudinal axis or curved spine 161 in that, when it is placed in contact with underlying body tissue MYO, it will have a concave orientation relative to said tissue. Depending on the parallel offset of a particular section plane from reference plane 163, the amount of concavity of the resulting longitudinal section curve 166 may differ from the concavity of curve 161, but in all instances a section curve with a concavity relative to the underlying tissue will result. If saddle-shaped surface 160 is cut by a section plane that is offset and parallel to plane 164, a transverse section curve, indicated generally as 167, will result. Transverse section curve 167 will be similar to transverse axis or curved rib section 162 in that, when it is placed in contact with underlying body tissue MYO, it will have a convex orientation relative to said tissue. Depending on the parallel offset of a particular section plane from reference plane 164, the amount of convexity of the resulting transverse section curve 167 may differ from the convexity of curve 162, but in all instances a section curve with a convexity relative to underlying tissue will result. Saddle-shaped surface 160 extends sufficiently lengthwise and sufficiently laterally, or transversely, to be able to accommodate the overall length and overall width of hand 10, respectively.

Figure 4A:
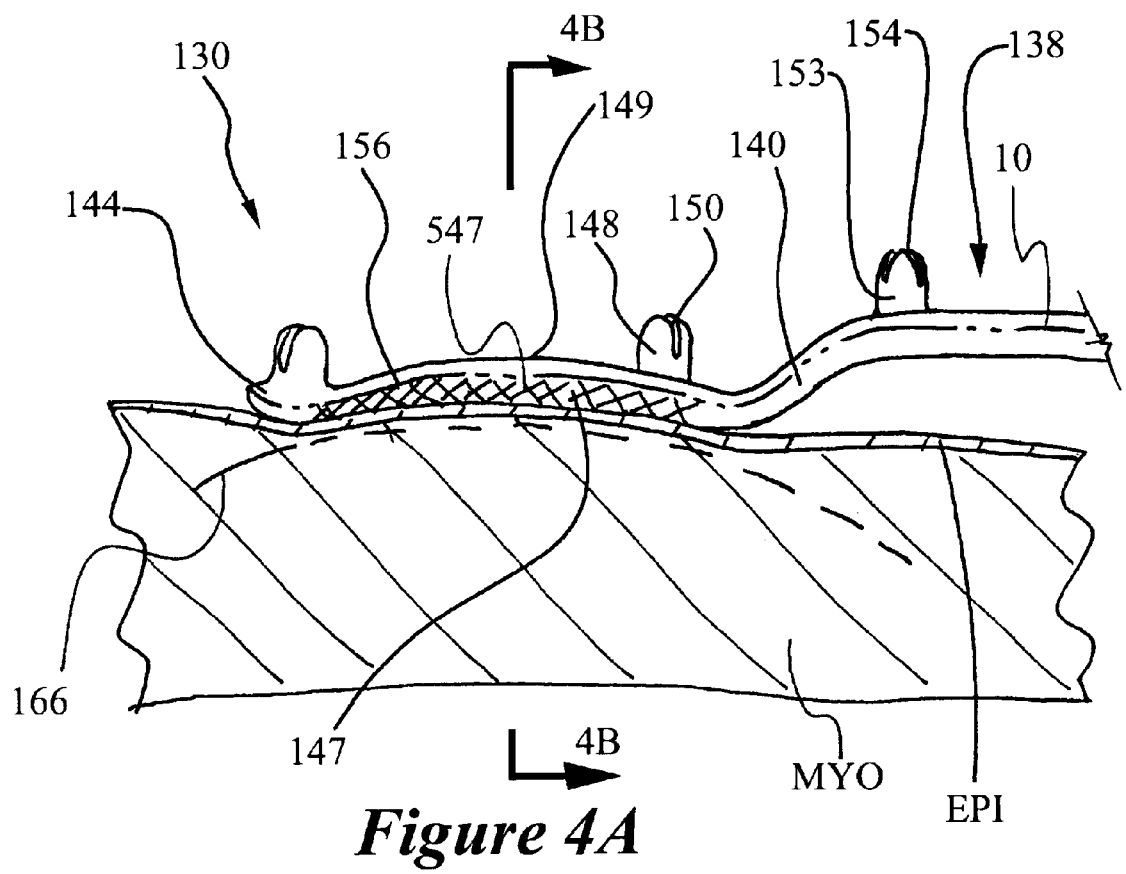
FIG. 4A is a partial side view of the bi-furcated hand illustrated in FIG. 2 depicting a body contacting portion in the nature of a finger having a concavity defined lengthwise along its contact surface.

Placing hand 10 to rest atop of surface 160, such that the notional longitudinal axis 136 of arterial window 134 is aligned and substantially coincident with curved spine 161, and such that curved rib section 162 traverses each of fingers 128 and 130 at their midspan location 149, a contact between saddle-shaped surface 160 and body-contacting surface 147 will result, at least over the medial portions of fingers 128 and 130. Therefore, each finger 128, 130 has a medial portion having a concavity defined lengthwise along its contact surface 147, the concavity being directed, in use, toward a body part. This concavity is intended to suitably conform to the natural curvature of a heart surface. FIG. 4A illustrates a side view of hand 10 placed in contact with myocardium tissue MYO. The myocardium tissue MYO is sectioned by a plane parallel to plane 163, within which also lies longitudinal section curve 166. Section curve 166 extends lengthwise along the contact surface 147 of finger 130, at about the mid-width location of said finger 130. For clarity, section curve 166 is offset slightly below the contact interface between finger 130 and the underlying body tissue, where it would normally be situated in this section plane. A thin layer of tissue is also illustrated to depict a top, or epicardium tissue layer EPI usually covering the patient's myocardium tissue.

Figure 4B:
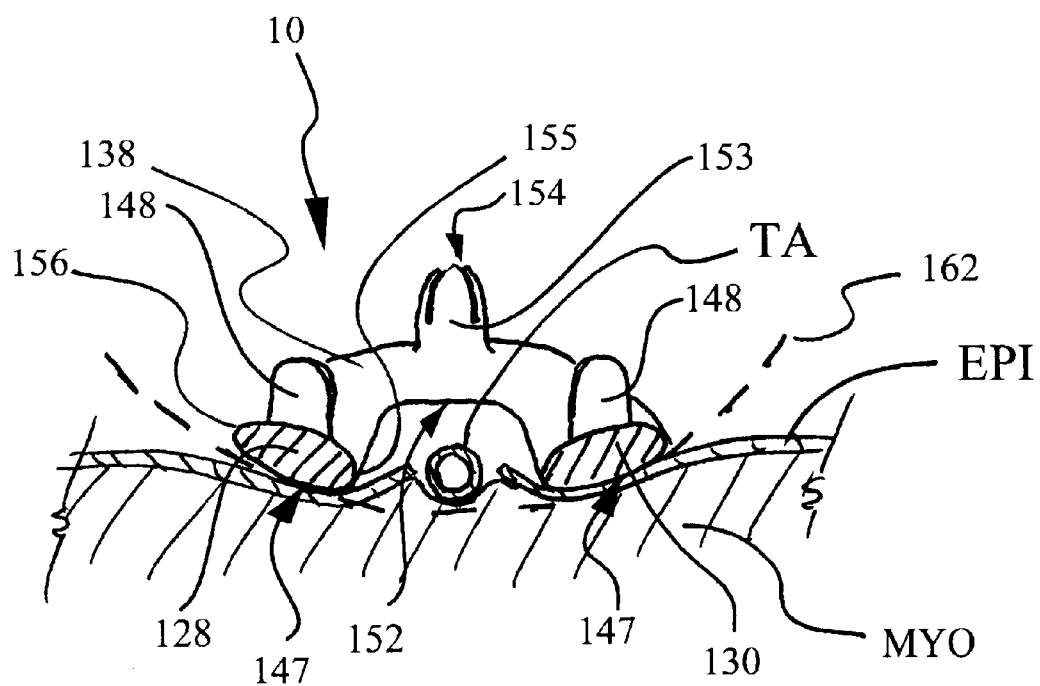
FIG. 4B is a partially sectioned front view of the bi-furcated hand illustrated in FIG. 4A depicting the cooperation of body contacting portions to define a convexity transversally through bi-furcated hand, and interrupted by an arterial window.

Referring again to hand 10 placed to rest atop of surface 160, in a manner described above. At any transverse section, generated by plane 164 or a plane that is offset parallel to plane 164, through each of the medial portions of fingers 128, 130, the contact surfaces 147 of each of the fingers 128, 130 cooperate to define a convexity. This convexity is interrupted by the width of the arterial window at this said transverse section, and the convexity being directed, in use, toward a body part. This is illustrated in FIG. 4B, which is a partially sectioned front view of hand 10 placed in contact with a myocardium tissue MYO, containing substantially therein a target artery TA. The epicardium layer of tissue EPI is illustrated subsequent to being incised lengthwise along the top of said target artery TA. Fingers 128, 130 and myocardium tissue MYO are sectioned by plane 164, within which also lies curved rib section 162. Curved section 162 extends transversely along the contact surfaces 147 of each of fingers 128, 130, at their midspan location 149. The contact surfaces 147 of each of fingers 128, 130 are generally aligned and substantially coincident with a different portion of curved section 162, and are spaced apart due to the interruption created by arterial window 134. As such, the contact surfaces 147 of each of fingers 128, 130 cooperate to define a convexity being directed, in use, toward a body part, said convexity being interrupted by an arterial window. This convexity is intended to isolate, expose, or extrude a portion of the immobilized myocardium tissue, containing a target artery, through the arterial window 134 of hand 10.

In this first embodiment, stepped portion 140, root portion 138, and distal tips 142, 144 do not come into contact with saddle-shaped surface 160, when hand 10 is placed to rest atop of surface 160, in a manner described above. Variant configurations are however possible with distal tips 142, 144 coming into contact with surface 160, or with stepped portion 140 flattened to bring root portion 138 into contact with said surface 160.

Referring now to FIG. 5A, an arterial window 134 is illustrated with a length LA and a width SA. The length of arterial window 134 is delineated partially by the medial portion of each finger 128 and 130, which are in contact with underlying body tissue, and partially by the yoke 132 and distal tips 142, 144 which are generally not in contact with underlying body tissue.

FIG. 5B illustrates a transverse section '5B—5B' through the contact surface 147 and exposed surface 146 of medial portions of fingers 128, 130. Exposed surface 146 is offset away from contact surface 147 by a certain thickness to give the required structural integrity to finger 128, 130 of hand 10, in order to be able to exert the required stabilization loads on a beating heart.

Surfaces 147 and 146 are joined by a curved spline or generously-radiused surface 151, inboard or inwardly towards arterial window, and by a curved spline or generously-radius surface 159 outboard or outwardly way from arterial window tending to reduce the likelihood of inducing tissue trauma to the contacted body tissue. As such, substantially elliptical cross-sections through fingers 128, 130 result.

Depending on the pressure applied to the hand 10 to compress underlying body tissue, or the amount of extrusion of underlying body tissue through the arterial window, the bottommost parts of radiused surface 151 and radiused surface 159 that are closest to contact surface 147, may also contact said underlying tissue and cooperate with said contacting surfaces 147. The uppermost parts of radiused surfaces 151 and 159, that are closest to exposed surface 146, will generally be exposed and free from contact with underlying contacted and immobilized body tissue, and as such will be considered an extension of exposed surface 146. Looking down on arterial window 134, in a direction substantially normal to plane 165, the opening of the arterial window is delineated or defined, in part, at least over the medial portion length of fingers 128, 130, by the edges of radiused surfaces 151. These inboard edges, one on each medial portion of fingers 128, 130, define an inner periphery 155, between which laterally spans at least a part of the arterial window. The remainder of the arterial window is defined by yoke 132, and more specifically, U-shaped cutout 152, which as illustrated in this first embodiment, is not in contact with underlying body tissue.

Similarly, a lateral dimension or a width of body contact member 10, across first and second body contact portions, or fingers 128, 130, is delineated or defined by the edges of radiused surfaces 159, at least over the medial portion length of fingers 128, 130. These outboard edges define an outer periphery 156. In transverse section '5B—5B', outer periphery 156 extends outwardly and upwardly away in height from inner periphery 155, and away from arterial window 134. The same applies for any other transverse section taken through medial portions of fingers 128, 130, where said transverse sections are generated by offsetting a section plane that is parallel to previously described plane 164. As such, the medial portions of fingers 128 and 130 assume an upwardly and outwardly-flaring, inverted skirt configuration, with inner periphery 155 defining the waist of the inverted skirt, and outer periphery defining the hemline or outer fringes of the inverted skirt. Approaching coronary stabilizer 1 towards a heart-like surface to be contacted, in a manner that the opening of its arterial window 134 is substantially tangent to said heart-like surface, inner periphery 155 of hand 10 will generally come into contact with heart tissue before outer periphery 156.

The medial portion of fingers 128 and 130 may have variant transverse cross-sections. For instance, FIG. 5C illustrates a transverse section through fingers 401, 402 with positive camber, airfoil-like cross-sections and contact surfaces 407. Outer periphery 406 extends in height away from inner periphery 405, and away from arterial window 134. FIG. 5D illustrates a transverse section through fingers 411, 412 with substantially S-shaped cross-sections and contact surfaces 417. Outer periphery 416 extends in height away from inner periphery 415, and away from arterial window 134. FIG. 5E illustrates a transverse section through fingers 421, 422 with negative camber, airfoil-like cross-sections and contact surfaces 427. Outer periphery 426 extends in height away from inner periphery 425, and away from arterial window 134. In each of these variants, a transverse section curve, indicated generally as TSC, has been illustrated. It may be observed that the contact surfaces 407 of each of fingers 401, 402 cooperate to define a substantial convexity being directed, in use, toward a body part, said substantial convexity being interrupted by an arterial window. Similarly, this also applies for contact surfaces 417 and 427. In each of the above variants, the medial portions of each of the fingers have a concavity defined lengthwise along their contact surface, the concavity being directed, in use, toward a body part.

Figure 6A:
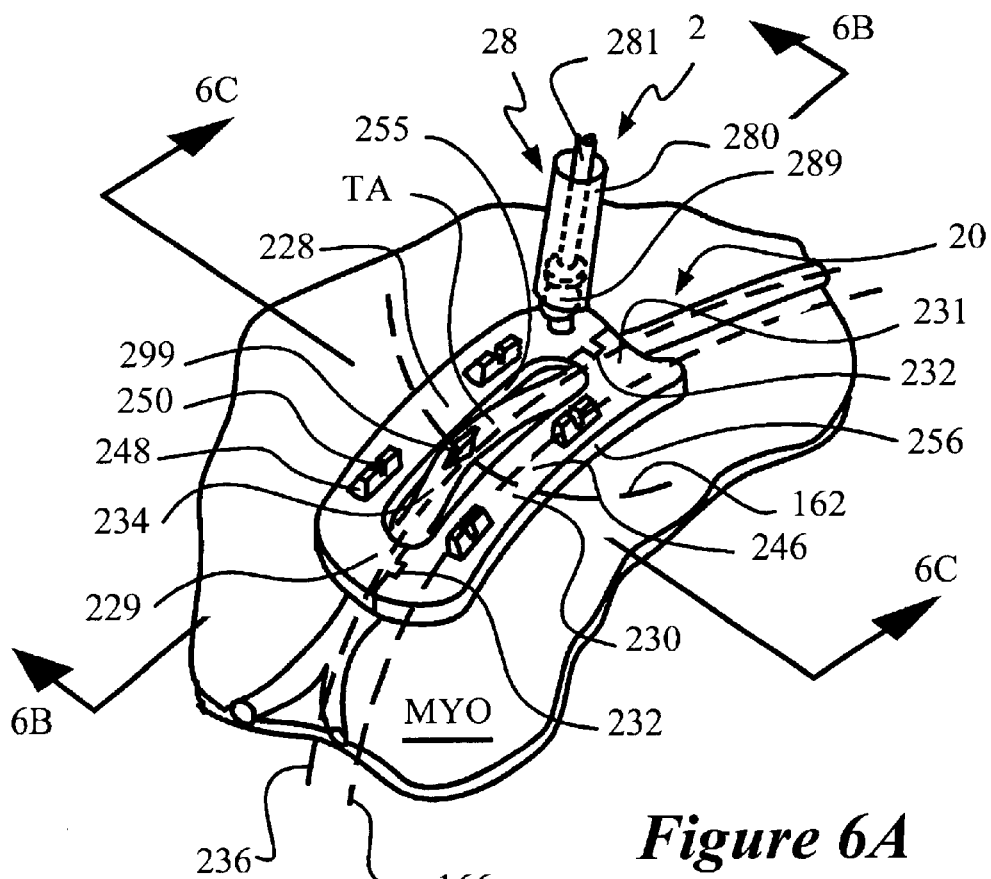
FIGS. 6A to 6C illustrate a variant of a body contact member according to a first embodiment of the present invention.
Figure 6B:
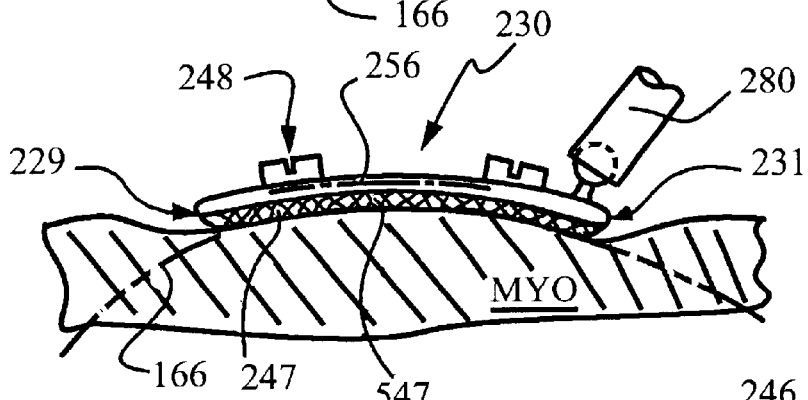
Figure 6C:
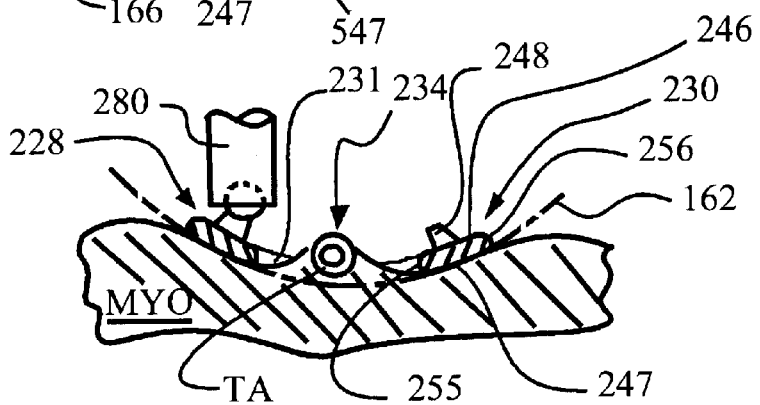

FIGS. 6A to 6C, illustrate an alternative embodiment to coronary stabilizer 1. Saddle-shaped coronary stabilizer 2 is comprised of a body-contacting member, in the nature of a plate 20, and a handle 28. Only a portion of handle 28 is illustrated in FIGS. 6A to 6C, that is, the portion closest to plate 20. The rest of handle 28 is very similar to handle 18, except for shaft 280 that is partially hollow over a part of its length, in order to be able to accommodate piston-type actuation member 281. Unlike handle 18, handle 28 is pivotingly connected to plate 20 through a wrist, or ball and socket joint 289. Said joint is rendered rigid through an actuation member 281, which is translatable along the hollow portion of shaft 280, and which fixes the relative position of said ball and socket components in joint 289. As illustrated, a ball portion is extending away from exposed surface 246 of plate 20. This ball portion interfaces with a socket surface configured partially in distal hollow portion of hollow shaft 280, and partially in the distal tip of actuation member 281. Such ball and socket joints exist in numerous varieties and are well known in the art.

Plate 20 is comprised of body-contacting portions in the nature of four strips 228, 229, 230, and 231, the strips defining between them a conduit window, or closed perimeter arterial window 234. First and second body-contacting portions, or longitudinal strips 228 and 230 are for placement to either side of a target coronary artery TA, with longitudinal axis of said target artery substantially aligned with the notional longitudinal axis 236 of arterial window 234. Third and fourth body-contacting portions, or lateral strips 229 and 231 are for placement transversely across of the target artery TA. As illustrated, lateral strips 229 and 231 are in contact with the underlying body tissue, in this case heart tissue represented as a top thin layer of epicardium tissue (labeled EPI) and a lower layer of myocardium tissue (labeled MYO). Often in the medical industry the surface of the heart is generally referred to as simply the myocardium, once the pericardium tissue has been extracted or peeled away, and also includes the thin layer normally covering the myocardium tissue. In the present application, the term myocardium MYO will generally refer to the surface of the heart, and will include the epicardium layer, unless the latter is specifically referred to.

Each of strips 228, 229, 230 and 231 has a first, or body-contacting surface 247, and a second, non-contacting, exposed surface 246 for facing away from the body contacted surface while in use. Each of longitudinal strips 228 and 230 has a medial portion generally spanning or extending between lateral strips 229 and 231. The body-contacting surface 247 generally extends over the said medial portion of each of longitudinal strips 228 and 230. Alternatively, plate 20 may be configured with either of lateral strips 229 and 231, or both, acting as opposing yokes with U-shaped cutouts. Lateral strips 229 and 231 may be substantially offset from longitudinal strips 228 and 230 in height away from contacted body tissue to avoid pressing down on and occluding the target artery TA which is straddled by longitudinal strips 228 and 230.

Plate 20 is preferably configured as a demountable assembly consisting of two, or more mating components. As illustrated, each of lateral strips 229 and 231 has a mechanical joint in the nature of tongue-in-groove joint 232. As such, two demountable and mating components result. The first such component consists of longitudinal strip 228 and a portion of each of lateral strips 229 and 231. The second such component consists of longitudinal strip 230 and the other mating portion of each of lateral strips 229 and 231. This demountable assembly permits the closed perimeter arterial window 234 to be opened of interrupted after the completion of a surgical intervention on target artery TA, such as a distal anastomosis to with an internal mammary artery, is performed. This opening of arterial window 234 allows the disengagement or retrieval of plate 20 from a newly-grafted bypass conduit which was anastomosed to target artery TA, at the site of the arteriotomy incision 299. A mechanical joint 232 may alternatively be configured in any two of the four strips 228, 229, 230, 231 to create a variant demountable plate 20. Two such mechanical joints 232 may also be configured in just one of the said four strips 228, 229, 230, 231. Variations in mechanical joint 232 are also possible. For instance, a pinned joint, a snap-fitted joint, a wire-fastened joint, a male-female interface joint, or other like mechanical joint may be used.

Plate 20 is preferably constructed from a polymeric material, approved for surgical use. Plate 20 may be plastic injection molded having an array of surgical wire attachment fittings, in the nature of slotted walls or slotted fences 248, formed integrally with plate 20 and extending outwardly from exposed surface 246. Each slotted fence 248 has at least one slot 250 for receiving an elastomeric vascular loop. As illustrated, each of longitudinal strips 228 and 230 has a pair of slotted fences 248, where said pair is spaced apart and generally aligned with the limits defining the medial portion of strips 228 and 230. One of the slotted fences 248 on strip 228 is not illustrated in FIG. 6C, in order to clearly illustrate mechanical joint 289.

Each of strips 228, 229, 230, 231 is advantageously contoured in a manner that will be discussed in greater detail below. Placing plate 20 to rest atop of saddle-shaped surface 160, such that the notional longitudinal axis 236 of arterial window 234 is aligned and substantially coincident with curved spine 161, and such that curved rib section 162 traverses each of longitudinal strips 228 and 230 at their midspan location, a contact between saddle-shaped surface 160 and body-contacting surface 247 of each of strips 228, 229, 230, and 231 will result (FIG. 6A). As such, each longitudinal strip 228, 230 has a medial portion having a concavity defined lengthwise along its contact surface 247, the concavity being directed, in use, toward a body part. This concavity is intended to suitably conform to the natural curvature of a heart surface. FIG. 6B illustrates a side view of plate 20 placed in contact with myocardium tissue MYO. The myocardium tissue MYO is sectioned by a plane parallel to plane 163, within which also lies longitudinal section curve 166. Section curve 166 extends lengthwise along the contact surface 247 of strip 230, at about the mid-width location of said strip 230. FIG. 6A illustrates the relative orientation of curved rib section 162 and longitudinal section curve 166 of saddle-shaped surface 160 to plate 20, if plate 20 is placed atop of saddle shaped surface 160 in the manner just described.

Referring again to plate 20 placed to rest atop of surface 160, in a manner described above. At any transverse section, generated by plane 164 or a plane that is offset parallel to plane 164, through each of the medial portions of longitudinal strips 228, 230, the contact surfaces 247 of each of the strips 228, 230 cooperate to define a convexity. This convexity is interrupted by the width of the arterial window 234 at this said transverse section, and the convexity being directed, in use, toward a body part. This is illustrated in FIG. 6C, which is a partially sectioned front view of plate 20 placed in contact with myocardium tissue MYO, containing substantially therein a target artery TA. Strips 228, 230 and myocardium tissue MYO are sectioned by plane 164 through section line '6B—6B' in FIG. 6A, within which also lies curved rib section 162. Curved section 162 extends transversely along the contact surfaces 247 of each of strips 228, 230, at their midspan location. The contact surfaces 247 of each of strips 228, 230 are generally aligned and substantially coincident with a different portion of curved section 162, and are spaced apart due to the interruption created by arterial window 234. As such, the contact surfaces 247 of each of strips 228, 230 cooperate to define a convexity being directed, in use, toward a body part, said convexity being interrupted by an arterial window. This convexity is intended to isolate, expose, or extrude a portion of the immobilized myocardium tissue, containing a target artery, through the arterial window 234 of plate 20.

Looking down on arterial window 234, in a direction substantially normal to plane 165, the opening of the arterial window is delineated or defined, in part, at least over the medial portion length of strips 228, 230, by inner periphery 255. The remainder of the arterial window is defined by the U-shaped inner edge of strips 229 and 231. Similarly, a lateral dimension or a width of plate 20, across first and second body contact portions, or strips 228, 230, is delineated or defined by outer periphery 256. In transverse section '6B—6B', outer periphery 256 extends in height away from inner periphery 255, and away from arterial window 234. The same applies for any other transverse section taken through medial portions of strips 228, 230, where said transverse sections are generated by offsetting a section plane that is parallel to previously described plane 164. As such, the medial portions of strips 228 and 230 assume an upwardly and outwardly-flaring, inverted skirt configuration, with inner periphery 255 defining the waist of the inverted skirt, and outer periphery defining the hemline or outer fringes of the inverted skirt. Approaching coronary stabilizer 2 towards a heart-like surface to be contacted, in a manner that the opening of its arterial window 234 is substantially tangent to said heart-like surface, inner periphery 255 of plate 20 will generally come into contact with said heart tissue before outer periphery 256.

Figure 8A:
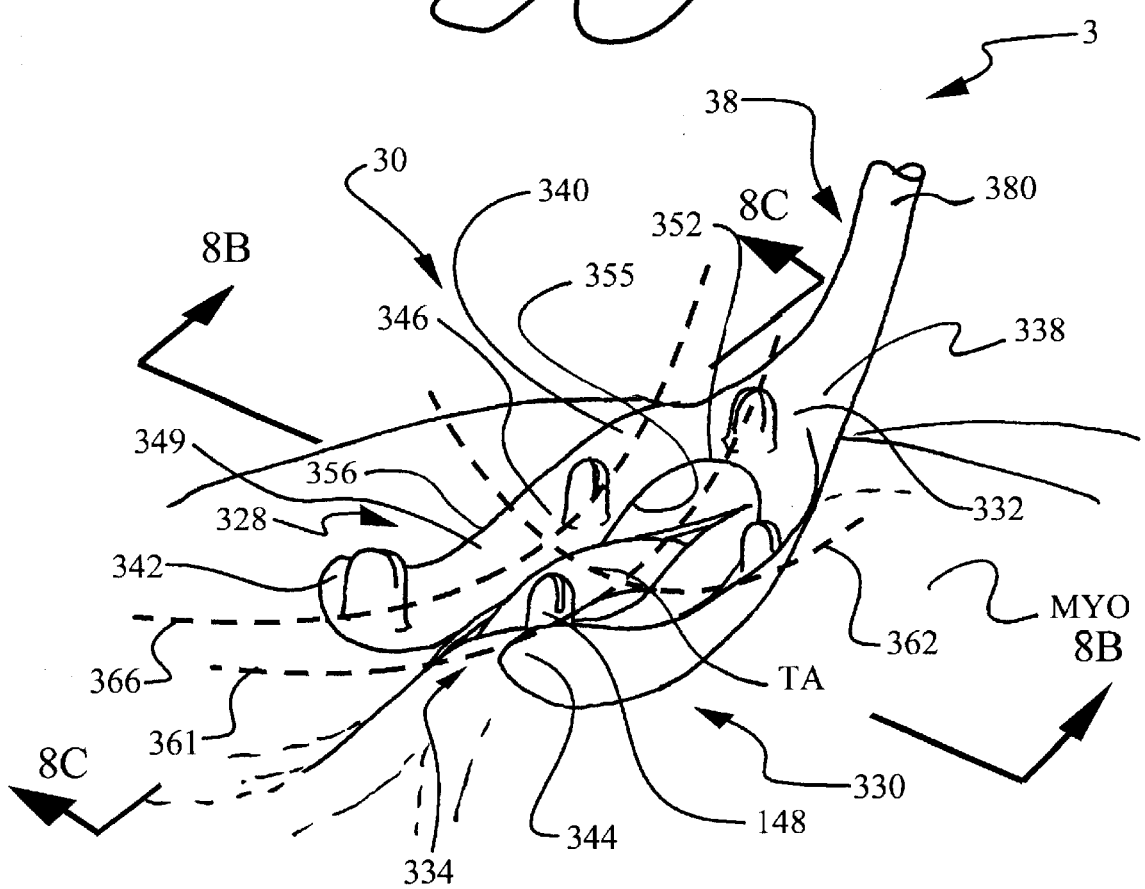
FIG. 8A is a partial perspective view of a coronary stabilizer with cup-shaped contact surface, according to a second embodiment of the present invention.

FIG. 8 illustrates a second embodiment according to the present invention. Coronary stabilizer 3 is a push-type tissue stabilizer that may tend to be suited for anterior coronary artery revascularizations on a beating heart, as described below. A push-type stabilizer is so named because, in operation, shaft 380 (partially illustrated) will tend to be in compression, when exerting a force to manipulation member (not shown) of handle 38 against, for example, a portion of the heart. A steep angled push-type handle, that is, one which is substantially perpendicular relative to contact member 30, will tend to have a greater proportion of its load in compression than a cantilever-like shallow angled push-type handle. A handle of this type will tend to extend away from the target artery in a direction that is generally forwardly of the target artery surface of the heart. This may tend to facilitate the engagement of shaft 380 in elbow joint 82 of articulated arm assembly 8, when contact member 30 is placed in contact with the anterior territory of a patient's heart surface.

Unlike coronary stabilizer 1 which is comprised of a substantially saddle-shaped contact member 10, coronary stabilizer 3 is comprised of a substantially cup-shaped contact member in the nature of bi-furcated hand 30. Hand 30 has first and second body-contacting portions in the nature of a pair of fingers 328 and 330 joined by a yoke 332, the fingers defining between them a conduit window, or arterial window indicated generally as 334. Yoke 332 has a tapering root portion 338 connected to shaft 380, and a bent, stepped portion 340 joining root portion 338 to the proximal ends of fingers 328 and 330. Root portion 338 is substantially offset from fingers 328, 330 in height away from contacted body tissue, in this case myocardium tissue MYO, to avoid pressing down on and occluding the target artery TA which is straddled by fingers 328, 330. U-shaped cut-out 352 is deep enough in stepped portion 340 to clear target artery TA straddled by said fingers. Fingers 328 and 330 have rounded distal tips 342 and 344 that are bent to stand away from the body contacted surface in use.

Fingers 328 and 330 are for placement to either side of target coronary artery TA, with the longitudinal axis of target artery TA substantially aligned with the notional longitudinal axis of arterial window 334. Each of the fingers 228 and 330 has a first, or body contacting surface 347, and a second, non-contacting, exposed surface 346 for facing away from the body contacted surface while in use. Each of the fingers 328 and 330 has a medial portion generally spanning or extending between rounded distal tip 342 or 344, and stepped portion 340. The body-contacting surface 347 generally extends over the said medial portion of each finger 328 and 330.

Figure 7:
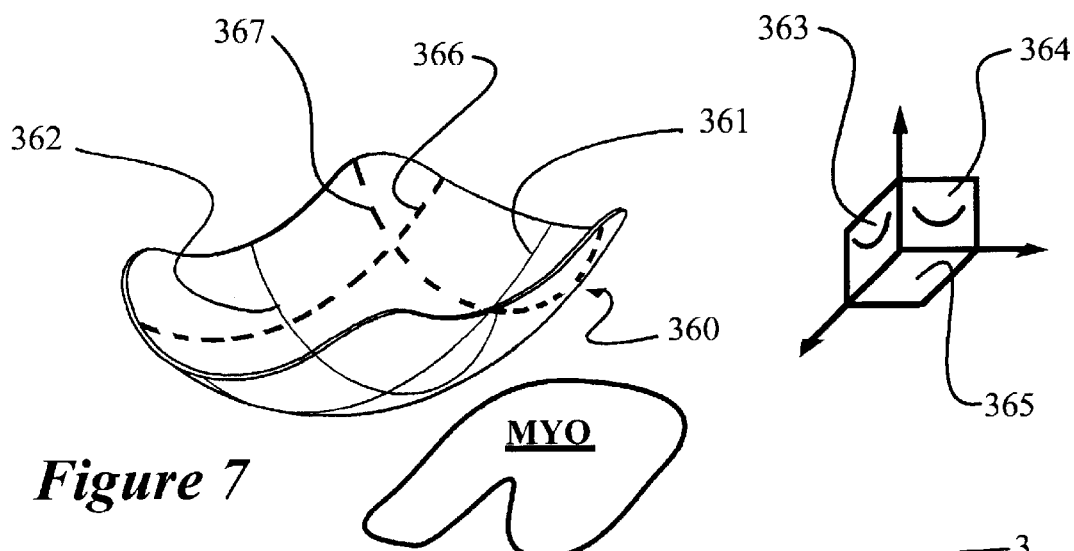
FIG. 7 is a schematic representation of a cup-shaped surface which helps define the body contact surface of a coronary stabilizer according to a second embodiment of the present invention.

As will be discussed in greater detail below, fingers 328 and 330 have contoured contact surfaces tending to maximize the extrusion of myocardium tissue through arterial window 334. With reference to FIG. 7, surface 360 depicts an infinitesimally-thin, substantially cup-shaped surface. Lengthwise, it is characterized or defined by a longitudinal axis, longitudinal contour, or curved spine 361, which also longitudinally bisects said surface 360. Widthwise, it is characterized by a transverse axis, transverse contour, or curved rib section 362, which also transversely bisects said surface 360. Curved spine 361 generally lies within a plane 363, and when surface 360 is placed in contact with an underlying body tissue, schematically illustrated and labeled MYO, it has a convex orientation relative to said tissue. Curved rib section 362 generally lies in another plane 364, and when surface 360 is placed in contact with body tissue MYO, it has a convex orientation relative to said tissue. A third plane 365, is also defined as being tangent to curved rib section 362 at the point of intersection between curved spine 361 and curved rib section 362. Planes 363, 364, and 365 are perpendicular to each other.

If cup-shaped surface 360 is cut by a section plane that is offset and parallel to plane 363, a longitudinal section curve, indicated generally as 366, will result. Longitudinal section curve 366 will be similar to longitudinal axis or curved spine 361 in that, when it is placed in contact with underlying body tissue MYO, it will have a convex orientation relative to said tissue. Depending on the parallel offset of a particular section plane from reference plane 363, the amount of convexity of the resulting longitudinal section curve 366 may differ from the convexity of curve 361, but in all instances a section curve with a convexity relative to the underlying tissue will result. If cup-shaped surface 360 is cut by a section plane that is offset and parallel to plane 364, a transverse section curve, indicated generally as 367, will result. Transverse section curve 367 will be similar to transverse axis or curved rib section 362 in that, when it is placed in contact with underlying body tissue MYO, it will have a convex orientation relative to said tissue. Depending on the parallel offset of a particular section plane from reference plane 364, the amount of convexity of the resulting transverse section curve 367 may differ from the convexity of curve 362, but in all instances a section curve with a convexity relative to underlying tissue will result. Cup-shaped surface 360 extends sufficiently lengthwise and sufficiently laterally, or transversely, to be able to accommodate the overall length and overall width of hand 30, respectively.

Figure 8B:
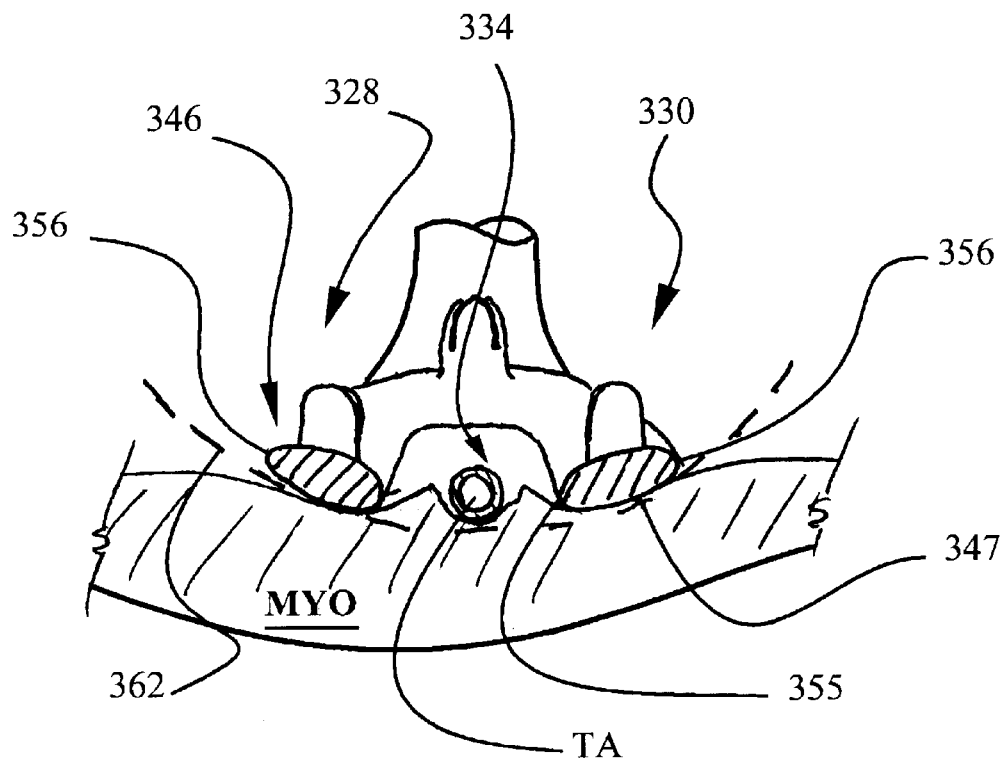
FIG. 8B is a partially sectioned front view of the bi-furcated hand illustrated in FIG. 8A depicting the cooperation of body contacting portions to define a convexity transversally through bi-furcated hand, and interrupted by an arterial window.
Figure 8C:
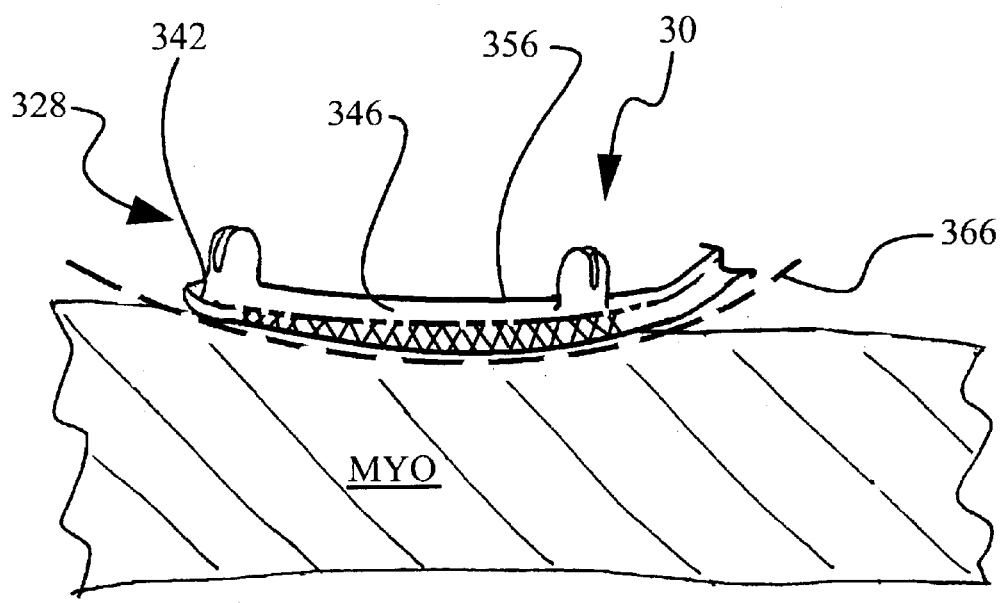
FIG. 8C is a partial side view of the bi-furcated hand illustrated in FIG. 8A depicting a body contacting portion in the nature of a finger having a convexity defined lengthwise along its contact surface.

Placing hand 30 to rest atop of surface 360, such that the notional longitudinal axis of arterial window 334 is aligned and substantially coincident with curved spine 361, and such that curved rib section 362 traverses each of fingers 328 and 330 at their midspan location 349, a contact between cup-shaped surface 360 and body-contacting surface 347 will result, at least over the medial portions of fingers 328 and 330. Therefore, each finger 328, 330 has a medial portion having a convexity defined lengthwise along its contact surface 347, the concavity being directed, in use, toward a body part. FIG. 8C illustrates a section view through finger 328 and myocardium tissue MYO, when hand 30 placed in contact with said tissue. Said section view is generated by a cutting plane that is offset parallel to plane 363, through section line '8C—8C' in FIG. 8A, within which also lies longitudinal section curve 366. Section curve 366 extends lengthwise along the contact surface 347 of finger 330, at about the mid-width location of said finger 330.

Referring again to hand 30 placed to rest atop of surface 360, in a manner described above. At any transverse section, generated by plane 364 or a plane that is offset parallel to plane 364, through each of the medial portions of fingers 328, 330, the contact surfaces 347 of each of the fingers 328, 330 cooperate to define a convexity. This convexity is interrupted by the width of the arterial window at this said transverse section, and the convexity being directed, in use, toward a body part. This is illustrated in FIG. 8B, which is a partially sectioned front view of hand 30 placed in contact with a myocardium tissue MYO, containing substantially therein a target artery TA. Fingers 328, 330 and myocardium tissue MYO are sectioned by plane 364 through section line '8B—8B' in FIG. 8A within which also lies curved rib section 362. Curved section 362 extends transversely along the contact surfaces 347 of each of fingers 328, 330, at their midspan location 349. The contact surfaces 347 of each of fingers 328, 330 are generally aligned and substantially coincident with a different portion of curved section 362, and are spaced apart due to the interruption created by arterial window 334. As such, the contact surfaces 347 of each of fingers 328, 330 cooperate to define a convexity being directed, in use, toward a body part, said convexity being interrupted by an arterial window. This convexity is intended to isolate, expose, or extrude a portion of the immobilized myocardium tissue, containing a target artery, through the arterial window 334 of hand 30.

Looking down on arterial window 334, in a direction substantially normal to plane 365, the opening of the arterial window is delineated or defined, in part, at least over the medial portion length of fingers 328, 330, by inner periphery 355. The remainder of the arterial window is defined by yoke 332, and more specifically, U-shaped cut-out 352, which as illustrated in this second embodiment, is not in contact with underlying body tissue. Similarly, a lateral dimension or a width of body contact member 30, across first and second body contact portions, or fingers 328, 330, is delineated or defined by outer periphery 356. In transverse section 8B—8B, outer periphery 356 extends in height away from inner periphery 355, and away from arterial window 334. The same applies for any other transverse section taken through medial portions of fingers 328, 330, where said transverse sections are generated by offsetting a section plane that is parallel to previously described plane 364. As such, the medial portions of fingers 328 and 330 assume an upwardly and outwardly-flaring, inverted skirt configuration, with inner periphery 355 defining the waist of the inverted skirt, and outer periphery defining the hemline or outer fringes of the inverted skirt. Approaching coronary stabilizer 3 towards a heart-like surface to be contacted, in a manner that the opening of its arterial window 334 is substantially tangent to said heart-like surface, inner periphery 355 of hand 30 will generally come into contact with said heart tissue before outer periphery 356.

Figure 9A:
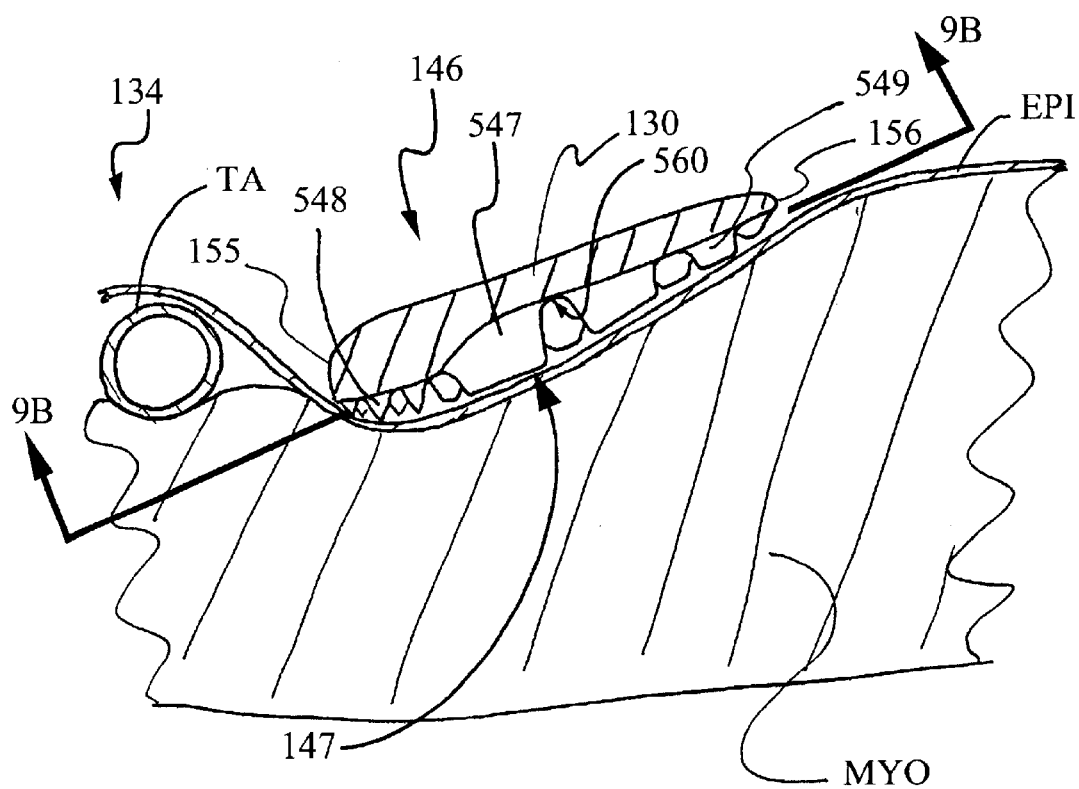
FIG. 9A is an enlarged transverse section view of the finger illustrated in FIG. 2, depicting a tissue-engaging texture of body contact surface.
Figure 9B:
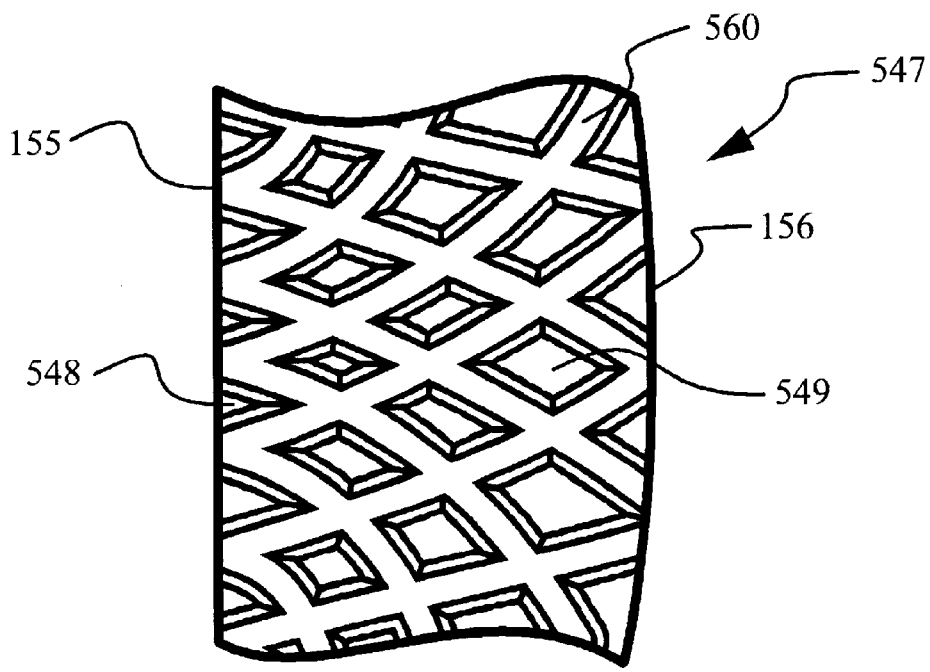
FIG. 9B is a true view of the body contacting surface illustrated in FIG. 9A depicting a tissue engaging texture with tractile gradient.

FIG. 9A illustrates an enlarged transverse section view through finger 130, depicting a tread or tissue-engaging texture 547 preferably disposed on contact surface 147. Tissue-engaging texture 547 is intended to improve the adherence of the underlying contacted heart tissue to the contact member 10 of coronary stabilizer 1. During a beating heart surgery, the pulsating effect of the heart may tend to induce slipping of the myocardium tissue relative to the said contact member, and even disengagement of said tissue from said contact member.

Texture 547 is comprised of an array of variably sized protrusions spaced apart by a series of depressions or grooves 560. These protrusions may be configured in a variety of shapes and geometries such as diamond-based truncated pyramids, for instance. A greater density (number per surface area) of smaller, finer, or sharper truncated pyramids 548 is arranged on contact surface 147, closest to inner periphery 155. As such, the density of grooves 560 is also generally greater closest to inner periphery 155. Moving laterally away from inner periphery 155 towards outer periphery 156, a lower density of progressively larger, blunter truncated pyramids 549 is encountered. The density of grooves 560 also decreases, thereby resulting in fewer depressions per surface area for the underlying tissue to penetrate. As such, the myocardium tissue closest to the arterial window tends to be gripped more positively or effectively by the contact member 10. This tends to improve the likelihood of a slip-free stabilization of the portion of myocardium tissue closest to the arterial window, thereby also tending to achieve a stable exposure of target artery TA accessed through said arterial window. The myocardium tissue closest to outer periphery 156 tends to be less effectively gripped by contact member 10. Consequently, contact surface 147 is configured with a tractive gradient, with the traction of the contact member on myocardium tissue generally increasing in a direction towards the arterial window, and towards the inner periphery 155. Said tractive gradient generally decreases in a direction towards the outer periphery 156 and away from arterial window 134. The tractive gradient also tends to provide a more gradual transition from the substantially immobile myocardium tissue, close to inner periphery 155, to the naturally beating mobile tissue located outwardly away from outer periphery 156.

Although tissue-engaging texture 547 is described in reference to coronary stabilizer 1, it is understood that it may exist on any contact surface of a coronary stabilizer according to the present invention. As well, variant geometries of protrusions characterizing texture 547 are also possible. For instance, an array of variably sized truncated cones, truncated cylinders, truncated domes, or other like protrusions may be used.

Figure 10A:
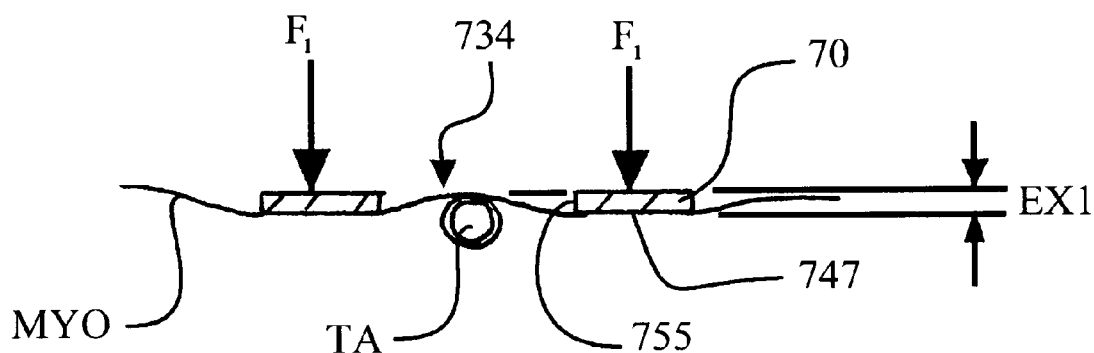
FIG. 10A is a diagrammatic representation of a tissue extrusion obtained when deploying a coronary stabilizer with a substantially planar body contacting surface.
Figure 10B:
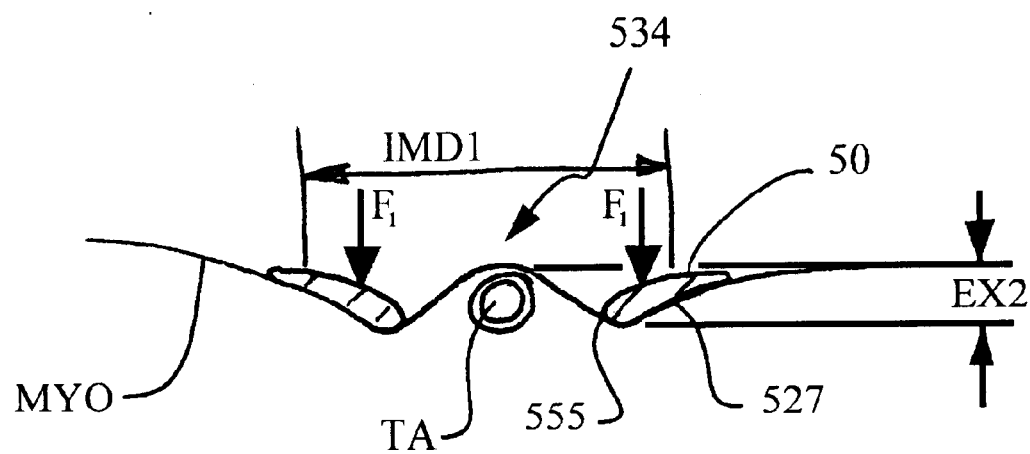
FIG. 10B is a diagrammatic representation of a tissue extrusion obtained when deploying the coronary stabilizer illustrated in FIG. 1.
Figure 10C:
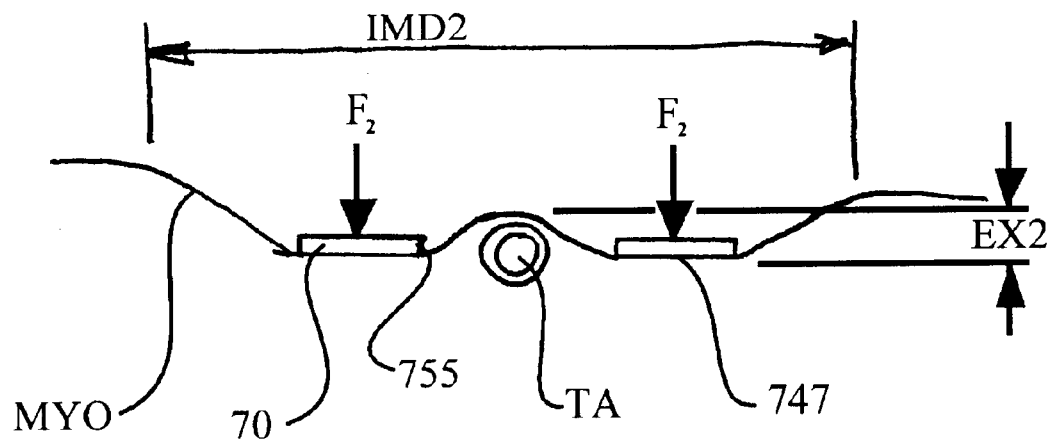
FIG. 10C is a diagrammatic representation of a tissue extrusion obtained when the coronary stabilizer illustrated in FIG. 10A is deployed with an increased stabilization force.
Figure 1:
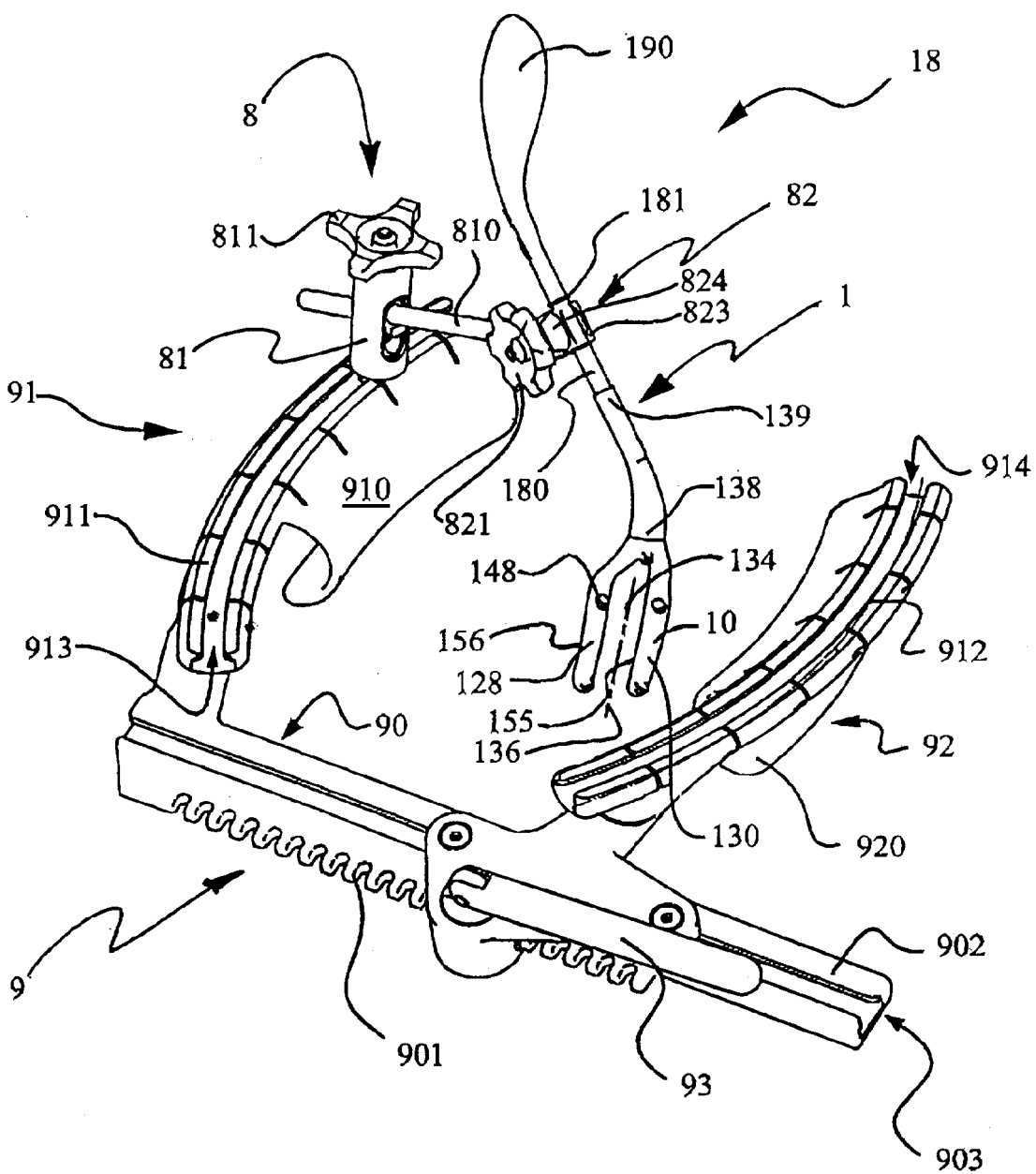
Figure 2:
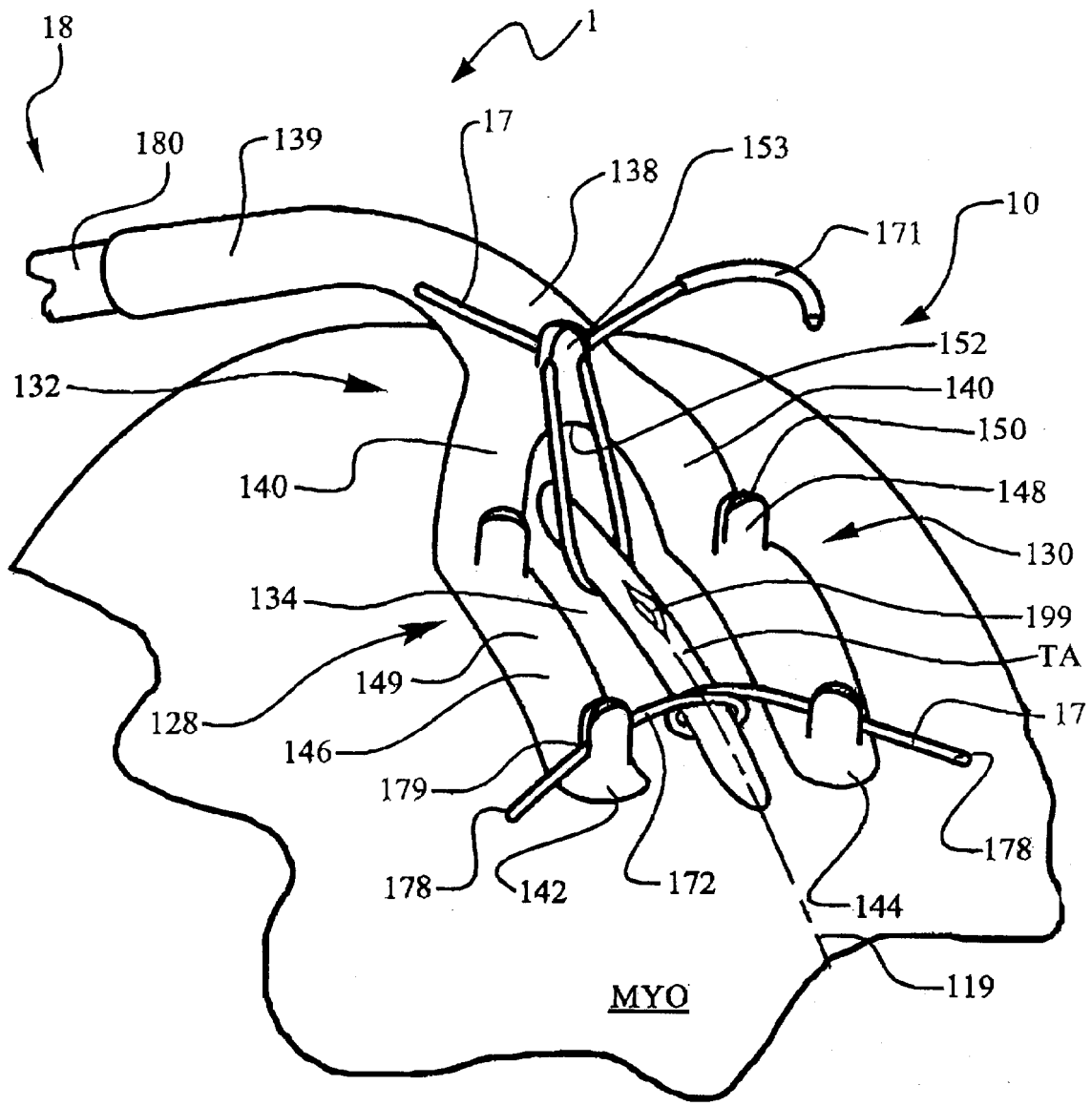

FIGS. 10A to 10C illustrate the effects of stabilizing a beating heart tissue with a conventional, substantially planar contact member 70 relative to an advantageously-contoured contact member, indicated generally as 50, according to the embodiments of the present invention. FIG. 10A illustrates the small and generally insignificant amount of myocardium tissue extrusion, EX1, which may be obtained through arterial window 734, when a coronary stabilizer with contact member 70 is placed in contact with said myocardium tissue. Extrusion EX1 is defined as the maximum protrusion of myocardium tissue MYO through arterial window 734, measured above contact surface 747, in the vicinity of its inner periphery 755. Extrusion EX1 is obtained when a first, hemodynamically-tolerable stabilization force F1 is exerted on the beating heart, by contact member 70. A small myocardium extrusion, such as EX1, tends to render more difficult the surgical interventions to target artery TA that will generally be performed through arterial window 734, especially with deep intramyocardial target coronary arteries. Referring to FIG. 10B, contacting and immobilizing a portion of the beating heart surface with an advantageously-contoured contact member 50, results in a larger, more significant myocardium tissue extrusion, EX2, through arterial window 534, when a similar stabilization force F1 is exerted on the beating heart by contact member 50. Extrusion EX2 is defined as the maximum protrusion of myocardium tissue MYO through arterial window 534, measured above contact surface 527, in the vicinity of its inner periphery 555. The larger, more significant extrusion EX2 tends to facilitate the surgical intervention on target artery TA. Referring to FIG. 10C, a significantly larger stabilization force F2 than force F1 tends to be required, if a similar extrusion EX2 is to be achieved with substantially planar contact member 70. This larger stabilization force F2 is not as likely to be well tolerated by the beating heart. As such, an increased compression of a heart chamber below the stabilization load applied by F2 tends to result, leading to potential distortions in the heart valvulature. This tends to induce an undesirable hemodynamic instability during the surgical procedure. For a desired extrusion EX2, contact member 70 will tend to substantially immobilize or inhibit a wider portion of myocardium tissue, IMD2, from beating naturally. In comparison, for a similar desired extrusion EX2, contact member 50 tends to inhibit a narrower portion of myocardium tissue, IMD1. As such, the outwardly-flaring inverted skirt configuration tends to allow the beating heart function to resume over a shorter lateral distance away from the arterial window and immobilized target artery TA therein. This tends to reduce the likelihood of compromising the natural beating heart function when a target artery TA is immobilized with contact member 50.

When compared to a substantially planar conventional stabilizer, the outwardly-flaring, inverted skirt configuration of contact member 50 engages the myocardium tissue in a wedge-like fashion. For a given stabilization force exerted by a contact member 50 on the beating heart, a greater localized compression tends to result in the portion of contacted myocardium tissue closest to target artery TA and inner periphery 555, unlike contact member 70 which tends to exert a smaller, substantially uniform compression over the entire contacted myocardium. Referring again to FIG. 10B, the resulting undulations or deflections in myocardium tissue, and the resulting extrusion of myocardium tissue proudly through arterial window 534, tends to enhance the lateral stability between contact member 50 and the portion of engaged or immobilized myocardium tissue, and also between contact member 50 and target artery TA. This is especially important during the immobilization of a body tissue which is beating, pulsating, or moving due to a physiologic response.

In broad terms, a surgical procedure for the use and deployment of a surgical apparatus with which the invention may be used during a coronary artery revascularization performed on a beating heart, preferably consists of:

(a) Performing a partial or midline sternotomy incision;
(b) Cauterizing any bleeding vessels subsequent to the sternotomy incision;
(c) Retracting the patient's ribcage through the deployment of chest retractor 9;
(d) Harvesting the required number and type of suitable bypass conduits such as saphenous vein, radial artery, or internal thoracic artery to be used in the revascularization of the target coronary artery;
(e) Incising the pericardium tissue that envelopes the beating heart to expose at least a portion of the underlying myocardium surface in the general vicinity of the target artery;
(f) Positioning and orienting of the beating heart within retracted chest cavity, in order to improve surgical access to a portion of myocardium containing substantially therein a target coronary artery;
(g) Positioning and orienting of coronary stabilizer 1 with respect to the portion of myocardium containing substantially therein a target coronary artery;
(h) Securing of coronary stabilizer 1 in the desired position and orientation relative to the chest retractor 9 through its engagement and securement in articulated arm assembly 8, which is itself engaged and secured relative to said chest retractor 9;

(i) Within arterial window 134, inserting needle 171 of vascular loop 17 into the myocardium tissue, and threading through said myocardium tissue a length of vascular loop 17, in a manner to at least partially encircle a target artery TA, and at a location upstream of intended arteriotomy incision 199;

(j) Applying a tension to each of segments 178 of vascular loop 17 and securing each of said segments into a different slot 150, or 154, in a manner to tend to enhance the extrusion of myocardium tissue through said arterial window, and constrict the target artery contained substantially therein;

(k) If required, readjusting the amount of target artery constriction by pulling vascular loop 17 through its engaged slots, in a manner to shorten or lengthen constricting length 172, in order to adequately restrict blood flow through target artery;

(l) Similarly, if preferred, engaging another vascular loop 17 in a location downstream of intended arteriotomy incision 199, and securing it to two slotted posts 148, on opposite sides of arterial window 134;

(m) Performing a surgical intervention on target artery TA in the nature of an arteriotomy incision 199;

(n) Performing a subsequent surgical intervention on target artery TA in the nature of a bypass graft anastomosis, between said target artery and said previously-harvested bypass conduit;

(o) Disengaging vascular loop(s) 17 from slotted post 148, or 153, in order to relieve imposed constriction on target artery;

(p) Verifying leakage at bypass graft anastomosis site;

(q) Verifying blood flow and patency through newly-grafted bypass conduit, for instance with Doppler ultrasonography;

(r) Once bypass graft anastomosis is deemed surgically acceptable, disengaging vascular loop(s) entirely from myocardium tissue, and disengaging coronary stabilizer 1 from the surface of the beating heart;

(s) In multivessel coronary artery bypass graft surgeries, repeat steps (f) to (r) above for other target coronary arteries requiring a coronary artery revascularization;

(t) Draining chest cavity and closing surgical patient as per standard protocol.

The coronary stabilizers 1, 2, 3 described above may also be deployed independently of the articulated arm assembly 8, and held instead by a surgical assistant, for instance.

Some of the features described above with reference to the embodiments of the present invention may also be applied to coronary stabilizers which employ a negative pressure suction force at a body contacting surface, to tend to improve the adherence or engagement of the contact member with the underlying contacted body tissue.

The above description of the embodiments of the present invention should not be interpreted in any limiting manner since variations and refinements are possible without departing from the spirit of the invention.

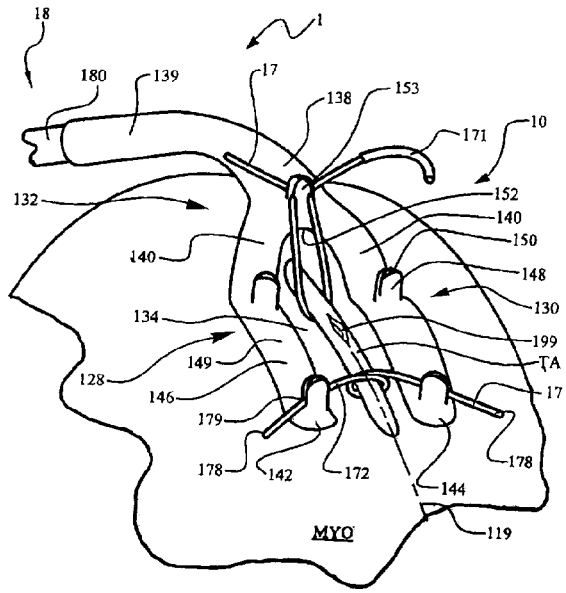

We claim:

1. A stabilizing implement for transmitting a generally rectilinear stabilizing force so as to locally stabilize a beating heart, said beating heart including a generally deformable myocardial tissue and defining a heart outer surface, said beating heart having a coronary vessel extending at least partially along said heart outer surface, said stabilizing implement comprising:

a generally elongated handle and a stabilizing base attached to said handle;

said stabilizing base including a pair of stabilizing plates, each of said stabilizing plates defining a plate contacting surface and a generally opposed plate free surface;

said plate contacting surface defining a selectively optionally plate contacting region for integrally contacting said heart outer surface;

each of said stabilizing plates having a generally elongated configuration and defining a plate longitudinal axis, a plate transversal axis, a plate first longitudinal end, a plate second longitudinal end, a plate first transversal edge and a generally opposed plate second transversal edge;

said stabilizing plates being positioned with their respective plate first transversal edges in a spaced relationship relative to each other so as to define a plate spacing therebetween, said plate spacing being configured and sized for accommodating at least a segment of said coronary vessel;

said stabilizing plates being configured, sized and positioned so as to locally stabilize said beating bean when applied on said heart outer surface with said stabilizing force;

at least one of said stabilizing plates being configured, sized and positioned so that a corresponding plate contacting region thereof, located generally adjacent said plate first transversal edge, deforms said myocardial tissue located adjacent said vessel so as to bias said vessel in a direction generally normal to said heart outer surface when said at least one stabilizing plate is applied on said heart outer surface with said stabilizing force;

said stabilizing implement being configured so that when a fraction of said stabilizing force is applied on one of said stabilizing plates, said faction of said stabilizing force is transmitted integrally to said heart outer surface through said plate contacting region, said plate contacting region contacting said heart surface directly;

whereby when said stabilizing base is applied to said heart outer surface with said predetermined stabilizing force and with said vessel located in said plate spacing, said stabilizing plates stabilize said beating heart adjacent said vessel and said corresponding plate contacting region increases the exposure of said vessel through said plate spacing by extrusion of myocardial tissue therein.

2. A stabilizing implement as recited in claim 1 wherein said plate contacting region of said at least one stabilizing plate is configured and sized so that when said plate contacting region is applied generally normally on said heart outer surface and said stabilizing force is exerted thereon, the pressure generated on said heart outer surface forms a pressure gradient oriented such that the pressure magnitude located adjacent said plate first transversal edge is greater than the pressure magnitude located adjacent said plate second transversal edge.

3. A stabilizing implement as recited in claim 1 wherein said plate contacting surface of said at least one stabilizer plate defines a plate first contacting region and a plate second contacting region, said plate first contacting region being positioned closer to said plate first transversal edge than said plate second contacting region, said plate contacting surface being interrupted by a surface spacing between adjacent plate first contacting region and plate second contacting region.

4. A stabilizing implement as recited in claim 2 wherein said plate contact surface of said at least one stabilizing plate is configured and sized so that when said plate contacting surface is applied on said heart outer surface, said plate first contacting region contacts said heart outer surface prior to said plate second contacting region contacting said heart outer surface.

5. A stabilizing implement as recited in claim 3 wherein said plate contact surface of said at least one stabilizing plate is configured and sized so that when said plate contacting surface is applied on said heart outer surface, said plate second contacting region only contacts said heart outer surface once said plate first contacting region has biased a predetermined portion of biased myocardial tissue into said plate spacing.

6. A stabilizing implement as recited in claim 1 wherein said contacting surface of said at least one of said stabilizing plates has a transversally substantially convex cross-sectional configuration, and also has a longitudinally substantially convex cross-sectional configuration; whereby said corresponding plate contacting surface has a generally two-dimensionally convex "spoon-back"-shaped configuration.

7. A stabilizing implement as recited in claim 1 wherein said contacting surface of said at least one of said stabilizing plates has a transversally substantially convex cross-sectional configuration, and also has a longitudinally substantially concave cross-sectional configuration; whereby said corresponding plate contacting surface has a generally "saddle"-shaped configuration.

8. A stabilizing implement recited in claim 7 wherein at least a portion of said corresponding plate contacting surface has a texture for engaging said heart outer surface.

9. A stabilizing implement recited in claim 8 wherein said texture is a tread having a tractive gradient.

10. A stabilizing implement as recited in claim 7 wherein said surgical implement further comprises a surgical wire attachment fitting mounted to said stabilizer base.

11. A stabilizing implement recited in claim 7 wherein said handle is pivotingly engaged to said stabilizer base through a joint, said joint made rigid by an actuator so as to lock said handle and said base in a predetermined spatial relationship.

12. A stabilizing implement as recited in claim 1 wherein both said stabilizing plates are configured, sized and positioned so that a corresponding plate contacting region thereof located generally adjacent said plate first transversal edge deforms said myocardial tissue located adjacent said vessel in between said plate spacing so as to bias said vessel in a direction generally normal to said heart outer surface when said stabilizing plates are applied on said heart outer surface with said predetermined pressure.

13. A stabilizing implement as recited in claim 12 wherein said plate contacting regions of both said stabilizing plates together define a generally transversally convex and interrupted base contacting surface for contacting said heart outer surface; said base contacting surface being configured, sized and positioned so that together said plate contacting regions deform said myocardial tissue located adjacent said vessel so as to bias said vessel in a direction generally normal to said heart outer surface when said stabilizing plates are applied on said heart outer surface with said stabilizing force, said stabilizing implement being configured so that when said stabilizing force is applied on said stabilizing plates, said stabilizing force is transmitted integrally to said heart outer surface through said base contacting surface, said base contacting surface contacting said heart surface directly; whereby when said stabilizing base is applied to said heart outer surface with said predetermined stabilizing force and with said vessel located in said plate spacing, said stabilizing plates stabilize said beating heart adjacent said vessel and said corresponding plate contacting regions increase the exposure of said vessel through said plate spacing by extrusion of myocardial tissue therein.

14. A stabilizing implement as recited in claim 13 wherein said base contacting surface has a generally parabolic configuration.

15. A stabilizing implement as recited in claim 14 wherein said base contacting surface defines an apex and wherein said apex is located in general alignment with said plate spacing.

16. A stabilizing implement as recited in claim 13 wherein said base contacting surface also has a generally longitudinally convex cross-sectional configuration; whereby said base contacting surface has a generally two-dimensionally convex "spoon-back"-shaped configuration.

17. A stabilizing implement as recited in claim 13 wherein said base contacting surface also has a generally longitudinally concave cross-sectional configuration; whereby said base contacting surface has a generally "saddle"-shaped configuration.

18. A stabilizing implement as recited in claim 13 wherein each of said plate contacting surfaces defines a plate first contacting region and a plate second contacting region, said plate first contacting region being positioned closer to said plate first transversal edge than said plate second contacting region, said base contacting surface being interrupted by said plate spacing and by a contacting region spacing between adjacent plate first and second contacting regions.

19. A stabilizing implement as recited in claim 18 wherein at least one of said stabilizing plates has a generally "S"-shaped cross-sectional configuration defining a first arcuate segment and a second arcuate segment, said first arcuate segment extending from said plate first transversal edge to said second arcuate segment and being generally convex so as to define said plate first contacting region; said second arcuate segment extending from said first arcuate segment in a direction leading towards said plate second transversal edge, said second arcuate segment being generally concave so that said plate second transversal edge defines said plate second contacting region.

20. A stabilizing implement for transmitting a generally rectilinear stabilizing force so as to locally stabilize a body tissue, said body tissue being generally deformable and having an exposed tissue surface, said body tissue having a target site extending at least partially along said exposed tissue surface, said stabilizing implement comprising:

a generally elongated handle and a stabilizing base attached to said handle;

said stabilizing base including a pair of stabilizing plates, each of said stabilizing plates defining a plate contacting surface and a generally opposed plate free space;

said plate contacting surface defining a plate contacting region for integrally contacting said exposed tissue surface;

each of said stabilizing plates having a generally elongated configuration and defining a plate longitudinal axis, a plate transversal axis, a plate first longitudinal end, a plate second longitudinal end, a plate first transversal edge and a generally opposed plate second transversal edge;

said stabilizing plates being positioned with their respective plate first transversal edges in a spaced relationship relative to each other so as to define a plate spacing therebetween, said plate spacing being configured and sized for accommodating at least a segment of said target site;

said stabilizing plates being configured, sized and positioned so as to locally stabilize said body tissue when applied on said exposed tissue surface with said stabilizing force;

at least one of said stabilizing plates being configured, sized and positioned so that a corresponding plate contacting region thereof, located generally adjacent said plate first transversal edge, deforms said body tissue located adjacent said target site so as to bias said target site in a direction generally normal to said exposed tissue surface when said at least one stabilizing plate is applied on said exposed tissue surface with said stabilizing force;

said stabilizing implement being configured so that when a fraction of said stabilizing force is applied on one of said stabilizing plates, said fraction of said stabilizing force is transmitted integrally to said exposed tissue surface through said plate contacting region, said plate contacting region contacting said exposed tissue directly;

whereby when said stabilizing base is applied to said exposed tissue surface with said predetermined stabilizing force and with said target site located in said plate spacing, said stabilizing plates stabilize said body tissue adjacent said target site and said corresponding plate contacting region increases the exposure of said target site through said plate spacing by extrusion of deformable body tissue therein.

\* \* \* \* \*

UNITED STATES PATENT AND TRADEMARK OFFICE
CERTIFICATE OF CORRECTION

| | | |
|---|---|---|
| PATENT NO. | : 6,488,618 B1 | |
| DATED | : December 3, 2002 | |
| INVENTOR(S) | : Paolitto, Anthony, Valentini, Valerio and Cartier, Raymond | |

It is certified that error appears in the above-identified patent and that said Letters Patent is hereby corrected as shown below:

<u>Title page,</u>
Item [30], Foreign Application Priority Data, please correct to include the following:
-- [30]        Foreign Application Priority Data
    April 16, 1999        [CA]        Canada………………….. 2269242 --

Delete title page and substitute therefor the attached title page.

Delete Drawing Sheets 1 and 2 and substitute therefor the attached Drawing Sheets 1 and 2.

Signed and Sealed this

First Day of July, 2003

JAMES E. ROGAN
*Director of the United States Patent and Trademark Office*

(12) United States Patent
Paolitto et al.

(10) Patent No.: US 6,488,618 B1
(45) Date of Patent: Dec. 3, 2002

(54) CORONARY STABILIZER FOR PERFORMING BEATING HEART SURGERY

(75) Inventors: Anthony Paolitto, St. Leonard; Valerio Valentini, Montreal; Raymond Cartier, Town of Mount Royal, all of (CA)

(73) Assignee: Coroneo, Inc., Montreal (CA)

(*) Notice: Subject to any disclaimer, the term of this patent is extended or adjusted under 35 U.S.C. 154(b) by 0 days.

(21) Appl. No.: 09/550,168

(22) Filed: Apr. 14, 2000

(51) Int. Cl.[7] .................................................. A61F 2/00
(52) U.S. Cl. ........................................................ 600/37
(58) Field of Search ........................ 600/37, 213, 232, 600/235, 231, 210, 204, 205, 228; 606/205, 207, 210; 81/418, 419, 424.5–426.5; 152/209; 36/59

(56) References Cited

U.S. PATENT DOCUMENTS

| | | | | |
|---|---|---|---|---|
| 5,529,101 A | * | 6/1996 | Croyle et al. ............... | 152/209 |
| 6,036,641 A | * | 5/2000 | Taylor et al. ............... | 600/231 |
| 6,063,021 A | * | 5/2000 | Hossain et al. ............. | 600/37 |
| 6,132,370 A | * | 10/2000 | Furnish et al. ............. | 600/235 |
| 6,213,941 B1 | * | 4/2001 | Benetti et al. ............. | 600/235 |
| 6,241,655 B1 | * | 6/2001 | Riess ........................... | 600/37 |

FOREIGN PATENT DOCUMENTS

WO    WO-98/27869    * 7/1998

* cited by examiner

*Primary Examiner*—Eric F. Winakur
*Assistant Examiner*—David McCrosky

(57) ABSTRACT

The present invention provides an improved coronary stabilizer for use in cardiac surgery, and more particularly during a coronary artery bypass graft (CABG) surgery performed directly on a beating heart. The coronary stabilizer is comprised of a body contact member and a handle. An opening or arterial window is provided in the body contact member, in order to allow surgical access to a target coronary artery which is exposed through said arterial window. In a first embodiment, the body contact member is a bifurcated hand comprising first and second body contacting portions, for placement alongside a target artery. Each of said body contacting portions is contoured to provide a coronary stabilizer with a substantially saddle-shaped body contacting surface, thereby tending to promote the extrusion of immobilized myocardium tissue through the arterial window generally disposed between first and second contacting portions. The coronary stabilizer according to this first embodiment preferably has a pull-type handle and is best suited to immobilize a posterior or inferior portion of the beating heart surface, during posterior coronary artery revascularizations. In a second embodiment, a coronary stabilizer with a substantially cup-shaped body contacting surface is provided and preferably configured with a push-type handle. It is best suited to immobilize an anterior portion of the beating heart surface, during anterior coronary artery revascularizations. The coronary stabilizers according to the present invention are preferably configured with an array of surgical wire attachment fittings for engaging an elastic surgical wire, that may be looped about a target artery, in order to create a substantially bloodless surgical field during a beating heart anastomosis. The contact surfaces of the coronary stabilizers preferably have a tread or tissue-engaging texture which may be configured to provide a tractive gradient.

20 Claims, 11 Drawing Sheets